US011944585B2

(12) United States Patent
Chase et al.

(10) Patent No.: US 11,944,585 B2
(45) Date of Patent: Apr. 2, 2024

(54) ADJUSTABLE COMPRESSION GARMENT

(71) Applicant: TACTILE SYSTEMS TECHNOLOGY, INC., Minneapolis, MN (US)

(72) Inventors: Daniel G. Chase, Menomonie, WI (US); Darren Jay Wennen, Edina, MN (US); Kristian Dior Gamble, Minneapolis, MN (US)

(73) Assignee: TACTILE SYSTEMS TECHNOLOGY, INC., Minneapolis, MN (US)

( * ) Notice: Subject to any disclaimer, the term of this patent is extended or adjusted under 35 U.S.C. 154(b) by 170 days.

(21) Appl. No.: 17/373,680

(22) Filed: Jul. 12, 2021

(65) Prior Publication Data

US 2021/0338520 A1    Nov. 4, 2021

Related U.S. Application Data

(63) Continuation of application No. 15/286,378, filed on Oct. 5, 2016, now Pat. No. 11,058,599.

(Continued)

(51) Int. Cl.
*A61H 9/00* (2006.01)
*A41D 1/00* (2018.01)
(Continued)

(52) U.S. Cl.
CPC ............. *A61H 9/0078* (2013.01); *A41D 1/00* (2013.01); *A61F 5/02* (2013.01); *A61F 5/3707* (2013.01);
(Continued)

(58) Field of Classification Search
CPC ...... A61F 5/02–03; A61F 5/3715–3753; A61F 5/30; A61F 5/32; A61F 5/34;
(Continued)

(56) References Cited

U.S. PATENT DOCUMENTS 1,608,239 A * 11/1926 Rosett ................. A61H 9/0078
128/DIG. 20
1,795,893 A    3/1931 Rosett
(Continued)

FOREIGN PATENT DOCUMENTS

CN    102429755 A    5/2012
EP    2 226 044 A2    9/2010
(Continued)

OTHER PUBLICATIONS

U.S. Appl. No. 29/576,157, filed Aug. 31, 2016, Chase et al.
(Continued)

*Primary Examiner* — Justine R Yu
*Assistant Examiner* — Alexander Morales
(74) *Attorney, Agent, or Firm* — Mueting Raasch Group

(57) ABSTRACT

Compression garments may include mitts and tightening apparatus to don, or put on, such compression garments. The mitts may be configured to receive a user's hand such that the user can move one or more portions of the garments using the mitts. The tightening apparatus may allow a user to selectively tighten or loosen the garments about the user's body portions. Once donned, the compression garments may apply pressure to one or more regions of the user's body such as, e.g., arm regions, shoulder regions, torso regions, and neck regions.

13 Claims, 14 Drawing Sheets

Related U.S. Application Data

(60) Provisional application No. 62/305,951, filed on Mar. 9, 2016, provisional application No. 62/281,706, filed on Jan. 21, 2016, provisional application No. 62/237,192, filed on Oct. 5, 2015, provisional application No. 62/237,200, filed on Oct. 5, 2015, provisional application No. 62/237,209, filed on Oct. 5, 2015.

(51) Int. Cl.
    *A61F 5/02* (2006.01)
    *A61F 5/37* (2006.01)
    *A61F 13/04* (2006.01)
    *A61F 13/12* (2006.01)
    *A61F 13/14* (2006.01)

(52) U.S. Cl.
    CPC .............. *A61F 13/04* (2013.01); *A61F 13/12* (2013.01); *A61F 13/14* (2013.01); *A41D 2400/322* (2013.01); *A61H 2201/0103* (2013.01); *A61H 2201/0192* (2013.01); *A61H 2201/1604* (2013.01); *A61H 2201/1609* (2013.01); *A61H 2201/1614* (2013.01); *A61H 2201/1619* (2013.01); *A61H 2201/1623* (2013.01); *A61H 2201/1645* (2013.01); *A61H 2201/165* (2013.01); *A61H 2201/1652* (2013.01); *A61H 2201/5002* (2013.01); *A61H 2201/5007* (2013.01); *A61H 2201/5071* (2013.01); *A61H 2201/5097* (2013.01); *A61H 2205/02* (2013.01); *A61H 2205/022* (2013.01); *A61H 2205/04* (2013.01); *A61H 2205/08* (2013.01); *A61H 2205/081* (2013.01); *A61H 2205/082* (2013.01); *A61H 2205/083* (2013.01); *A61H 2205/084* (2013.01)

(58) Field of Classification Search
    CPC ........ A61F 5/37; A61F 5/012; A61F 5/05816; A41D 1/04; A41D 13/012; A41D 13/0155; A41D 2400/14; A41D 2600/102; A41D 7/003; A41D 13/018; A61H 9/0078; A61H 2201/0192; A61H 2201/5071; A61H 2205/04; A61H 2201/5002; A61H 2201/1623; A61H 2201/1619; A61H 2201/1609; A61H 2201/1604; A61H 2205/084; A61H 2201/1614; A61H 2201/5097; A61H 2205/022; A61H 2201/165; A61H 2205/083; A61H 2205/081; A61H 2205/082; A61H 2201/0103; A61H 2205/02; A61H 2201/1645; A61H 2205/08; A61H 2201/1652; A61H 2201/5007
    USPC ........ 602/13, 19; 128/869, 873–875; 2/2.17, 2/462–464, 6.2, 70, 102, 124, 160, 913, 2/249, 250, 323, 325
    See application file for complete search history.

(56) References Cited

U.S. PATENT DOCUMENTS

| | | |
|---|---|---|
| 2,676,587 A * | 4/1954 | Corcoran ............ A61H 9/0078 601/148 |
| 2,823,668 A | 2/1958 | Van Court et al. |
| 3,159,160 A | 12/1964 | Ullom |
| 3,397,688 A | 8/1968 | Gottfried |
| 3,695,593 A | 5/1972 | Vail |
| 4,210,147 A | 7/1980 | Nestor et al. |
| 4,765,338 A | 8/1988 | Turner et al. |
| 4,884,295 A | 12/1989 | Cox |
| D307,054 S | 4/1990 | Johnson, Jr. |
| 4,940,045 A | 7/1990 | Cromartie |
| 5,014,365 A | 5/1991 | Schulz |
| 5,031,246 A | 7/1991 | Kronenberger |
| 5,033,461 A | 7/1991 | Young et al. |
| 5,038,765 A | 8/1991 | Young et al. |
| 5,039,247 A | 8/1991 | Young et al. |
| 5,046,490 A | 9/1991 | Young et al. |
| 5,083,553 A | 1/1992 | Stevenson et al. |
| 5,188,587 A | 2/1993 | McGuire |
| 5,205,815 A | 4/1993 | Saunders |
| 5,215,517 A | 6/1993 | Stevenson et al. |
| 5,314,455 A | 5/1994 | Johnson, Jr. et al. |
| 5,334,134 A | 8/1994 | Saunders |
| 5,349,702 A | 9/1994 | Runckel |
| 5,383,844 A | 1/1995 | Munoz et al. |
| 5,399,150 A | 3/1995 | Saunders |
| 5,407,420 A | 4/1995 | Bastyr et al. |
| 5,449,379 A | 9/1995 | Hadtke |
| 5,466,250 A | 11/1995 | Johnson, Jr. et al. |
| 5,536,246 A * | 7/1996 | Saunders ................ A61F 5/028 602/19 |
| 5,628,725 A | 5/1997 | Ostergard |
| 5,697,962 A | 12/1997 | Brink et al. |
| D389,584 S | 1/1998 | Leventhal et al. |
| 5,733,321 A | 3/1998 | Brink |
| 5,741,220 A | 4/1998 | Brink |
| 5,911,612 A | 6/1999 | Steger |
| 5,921,946 A | 7/1999 | Tillinghast et al. |
| 5,976,099 A | 11/1999 | Kellogg |
| 6,030,412 A | 2/2000 | Klatz et al. |
| 6,110,133 A | 8/2000 | Ritts |
| 6,126,683 A | 10/2000 | Momtahemi |
| 6,179,796 B1 | 1/2001 | Waldridge |
| 6,182,288 B1 * | 2/2001 | Kibbee .................... F41H 1/02 2/2.5 |
| 6,338,723 B1 | 1/2002 | Carpenter |
| 6,436,064 B1 | 8/2002 | Kloecker |
| 6,551,280 B1 | 4/2003 | Knighton et al. |
| 6,592,535 B2 | 7/2003 | Ravikumar |
| 6,645,165 B2 | 11/2003 | Waldridge et al. |
| 6,860,862 B2 | 3/2005 | Waldridge et al. |
| 6,936,021 B1 | 8/2005 | Smith |
| 6,966,884 B2 | 11/2005 | Waldridge et al. |
| 7,044,924 B1 | 5/2006 | Roth et al. |
| 7,156,818 B2 | 1/2007 | Salmon et al. |
| D538,509 S | 3/2007 | Silverman |
| D554,225 S | 10/2007 | Peterson |
| 7,311,687 B2 | 12/2007 | Hoffmeier et al. |
| 7,396,345 B2 | 7/2008 | Knighton et al. |
| 7,563,236 B2 | 7/2009 | Kazmierczak et al. |
| 7,591,050 B2 | 9/2009 | Hammerslag |
| 7,631,382 B2 | 12/2009 | Dibenedetto et al. |
| 7,681,249 B2 * | 3/2010 | Oliver .................... B64D 10/00 2/102 |
| 7,691,084 B2 | 4/2010 | Knighton et al. |
| 7,698,909 B2 | 4/2010 | Hannula et al. |
| 7,749,181 B2 | 7/2010 | Simmons et al. |
| 7,771,376 B2 | 8/2010 | Roth et al. |
| 7,887,501 B2 | 2/2011 | Riordan et al. |
| 7,947,003 B2 | 5/2011 | Bonnefin et al. |
| 7,959,591 B2 | 6/2011 | Powers et al. |
| 7,967,765 B2 | 6/2011 | Nathanson |
| 8,046,937 B2 | 11/2011 | Beers et al. |
| 8,096,964 B1 | 1/2012 | Bruehwiler et al. |
| 8,147,438 B2 | 4/2012 | Livolsi et al. |
| 8,226,698 B2 | 7/2012 | Edelman et al. |
| 8,273,114 B2 | 9/2012 | Wasowski |
| 8,381,362 B2 | 2/2013 | Hammerslag et al. |
| 8,517,965 B2 | 8/2013 | Doty et al. |
| 8,591,440 B2 | 11/2013 | Logue et al. |
| D694,957 S | 12/2013 | Barker et al. |
| 8,597,219 B2 | 12/2013 | Hargrave et al. |
| D698,031 S | 1/2014 | Viner et al. |
| 8,641,654 B2 | 2/2014 | Verkade et al. |
| 8,667,613 B2 | 3/2014 | Blakely et al. |
| D714,022 S | 9/2014 | Mong et al. |
| 9,114,257 B2 | 8/2015 | Helfer et al. |

(56) References Cited

U.S. PATENT DOCUMENTS

| | | | |
|---|---|---|---|
| D744,202 S | 12/2015 | Brown | |
| 9,320,307 B2 | 4/2016 | Berns | |
| D770,730 S | 11/2016 | Borovicka | |
| D777,380 S | 1/2017 | Win | |
| D791,441 S | 7/2017 | Van Disseren | |
| D803,482 S | 11/2017 | Greenblat et al. | |
| D834,208 S | 11/2018 | Wennen et al. | |
| 10,492,974 B2 * | 12/2019 | Chase | A61H 1/008 |
| 10,576,234 B2 | 3/2020 | Brown et al. | |
| 10,589,048 B2 | 3/2020 | Garshow et al. | |
| 10,765,160 B2 | 9/2020 | Page | |
| D919,240 S | 5/2021 | Urban | |
| 11,058,599 B2 * | 7/2021 | Chase | A61F 13/14 |
| 11,166,868 B2 * | 11/2021 | Wennen | A61F 5/02 |
| D939,194 S | 12/2021 | Wallace | |
| D955,054 S | 6/2022 | Sonntag | |
| D961,195 S | 8/2022 | Garcia | |
| 11,432,965 B2 | 9/2022 | Kantor et al. | |
| D968,763 S | 11/2022 | Scher | |
| 11,517,058 B2 | 12/2022 | Moon et al. | |
| 2003/0032905 A1 | 2/2003 | Waldridge et al. | |
| 2003/0199922 A1 | 10/2003 | Buckman | |
| 2003/0220594 A1 * | 11/2003 | Halvorson | A61F 5/03 |
| | | | 602/19 |
| 2005/0143683 A1 | 6/2005 | Waldridge | |
| 2005/0148918 A1 | 7/2005 | Nathanson | |
| 2005/0197607 A1 | 9/2005 | Brown | |
| 2006/0000478 A1 | 1/2006 | Taylor | |
| 2006/0156517 A1 | 7/2006 | Hammerslag et al. | |
| 2006/0200057 A1 | 9/2006 | Sterling | |
| 2007/0161932 A1 | 7/2007 | Pick et al. | |
| 2007/0169378 A1 | 7/2007 | Sodeberg et al. | |
| 2008/0222771 A1 | 9/2008 | Natonson | |
| 2008/0245361 A1 | 10/2008 | Brown | |
| 2008/0319362 A1 * | 12/2008 | Joseph | A61F 13/04 |
| | | | 602/7 |
| 2009/0254014 A1 | 10/2009 | Son | |
| 2010/0228171 A1 | 9/2010 | Waldridge | |
| 2011/0009793 A1 | 1/2011 | Lucero et al. | |
| 2011/0071447 A1 | 3/2011 | Liu et al. | |
| 2011/0087142 A1 | 4/2011 | Ravikumar et al. | |
| 2011/0172579 A1 | 7/2011 | Chiu et al. | |
| 2011/0178447 A1 | 7/2011 | Helfer et al. | |
| 2011/0257463 A1 | 10/2011 | Nour et al. | |
| 2012/0004587 A1 | 1/2012 | Nickel et al. | |
| 2012/0150086 A1 | 6/2012 | Cohen | |
| 2012/0179084 A1 | 7/2012 | Lipshaw et al. | |
| 2012/0197160 A1 | 8/2012 | Reinhardt | |
| 2013/0012847 A1 | 1/2013 | Lowe et al. | |
| 2013/0012856 A1 | 1/2013 | Hammerslag et al. | |
| 2013/0079854 A1 | 3/2013 | Wasowski | |
| 2013/0197413 A1 | 8/2013 | Hoffmeier et al. | |
| 2013/0211300 A1 | 8/2013 | Verkade et al. | |
| 2013/0269219 A1 | 10/2013 | Burns et al. | |
| 2013/0345612 A1 | 12/2013 | Bannister et al. | |
| 2014/0018752 A1 | 1/2014 | Shuler | |
| 2014/0033402 A1 | 2/2014 | Donnadieu et al. | |
| 2014/0094728 A1 | 4/2014 | Soderberg et al. | |
| 2014/0123449 A1 | 5/2014 | Soderberg et al. | |
| 2014/0222121 A1 | 8/2014 | Spence et al. | |
| 2014/0276271 A1 * | 9/2014 | Stryker | A61H 23/04 |
| | | | 601/107 |
| 2015/0119775 A1 | 4/2015 | Gildersleeve et al. | |
| 2015/0157484 A1 | 6/2015 | Ex-Lubeskie et al. | |
| 2017/0209332 A1 | 7/2017 | Chase et al. | |
| 2017/0303607 A1 | 10/2017 | Iser et al. | |

FOREIGN PATENT DOCUMENTS

| | | |
|---|---|---|
| EP | 2 462 905 B1 | 11/2013 |
| EP | 1 703 871 B1 | 5/2015 |
| EP | 2 339 998 B1 | 5/2015 |
| EP | 2 613 745 B1 | 6/2015 |
| EP | 2 248 493 B1 | 9/2015 |
| FR | 2 624 003 A1 | 11/1988 |
| FR | 2 939 642 A1 | 6/2010 |
| GB | 699152 | 10/1953 |
| GB | 2 213 041 A | 8/1989 |
| JP | 3139689 U | 2/2008 |
| JP | 2010-126855 A | 6/2010 |
| JP | 2010-158319 A | 7/2010 |
| WO | WO 03/041621 A1 | 5/2003 |
| WO | WO 2007/014242 A1 | 2/2007 |
| WO | WO 2008/033963 A2 | 3/2008 |
| WO | WO 2014/151902 A1 | 9/2014 |
| WO | WO 2014/159706 A2 | 10/2014 |
| WO | WO 2015/038822 A1 | 3/2015 |
| WO | WO 2015/050897 A1 | 4/2015 |
| WO | WO 2015/117132 A1 | 8/2015 |

OTHER PUBLICATIONS

U.S. Appl. No. 29/576,182, filed Aug. 31, 2016, Chase et al.
U.S. Appl. No. 15/284,858, filed Oct. 4, 2016, Wennen et al.
U.S. Appl. No. 15/284,870, filed Oct. 4, 2016, Wennen et al.
U.S. Appl. No. 15/284,888, filed Oct. 4, 2016, Wennen et al.
U.S. Appl. No. 15/319,179, filed Dec. 15, 2016, Chase et al.
U.S. Appl. No. 15/411,003, filed Jan. 20, 2017, Wennen et al.
U.S. Appl. No. 15/411,059, filed Jan. 20, 2017, Chase et al.
U.S. Appl. No. 29/595,538, filed Feb. 28, 2017, Chase et al.
U.S. Appl. No. 29/596,757, filed Mar. 10, 2017, Wennen et al.
[European Patent Office] Patent Application No. PCT/US2016/055575, filed Oct. 5, 2016; [International Search Report / Written Opinion] dated Dec. 21, 2016; 11 pages.
PCT/US2016/055575, filed Oct. 5, 2016; International Preliminary Report on Patentability, dated Apr. 19, 2018; 7 pages.
FM01, <https://www.lipoelasticshop.com/fm-01?gclid=EAlaIQobChMizv3uzYbz_AIVBrbICh3y6APWEAkYASABEgLCIfD_BwE>, 2023.
Compression mask Facelift, <https://www.medicalexpo.com/prod/euromi/product-68435-865849.html>, 2023.
Office Action dated Feb. 6, 2023; 19 pages. U.S. Appl. No. 29/717,875.

* cited by examiner

ADJUSTABLE COMPRESSION GARMENT

This application is a continuation of U.S. patent application Ser. No. 15/286,378 filed Oct. 5, 2016, entitled "Adjustable Compression Garment" which claims the benefit of U.S. Provisional Application No. 62/237,192, filed Oct. 5, 2015, and entitled "Head and Neck Compression Therapy System," U.S. Provisional Application No. 62/237,200, filed Oct. 5, 2015, and entitled "Static and Dynamic Compression Therapy System," U.S. Provisional Application No. 62/237,209, filed Oct. 5, 2015, and entitled "Head and Neck Compression Garment," U.S. Provisional Application No. 62/281,706 filed Jan. 21, 2016, and entitled "Compression Garment System," and U.S. Provisional Application No. 62/305,951, filed Mar. 9, 2016, and entitled "Mitt For Compression Garments," each of which are incorporated herein in their entireties.

The present disclosure relates generally to the use of compression garments including mitts and tightening apparatus to don, or put on, such compression garments. Once donned, the compression garments may apply pressure to one or more regions of a portion of a body such as, e.g., arm regions, shoulder regions, torso regions, and neck regions.

Various types of compression garments may be used, for example, for treatment of lymphedema, edema, wound healing, etc. For example, garments may include inflatable chambers or cells (or other actuatable elements) to provide therapy to patients and may be positioned about any one or more body portions of a person or animal. Specifically, the garments may be positioned about body portions that exhibit swelling due to a build-up of lymph and that would benefit from compression therapy provided by the garments. For example, such chambers or cells may be inflatable to one or more different pressures in a variety of sequences to provide the therapy to the patient by moving lymph from one region to another. In other words, such compression garments may be placed around at least a portion of an individual's body for use in applying pressure to the body at an affected extremity. These compression garments may be donned (e.g., put on) and doffed (e.g., taken off) by patients themselves or with help from others.

SUMMARY

The exemplary garments described herein may include one or more mitts and one or more tightening apparatuses to assist a user in donning the exemplary garments. The mitts may define an opening to receive a hand of the user to move one or more portions of the garments about the user's body. The mitts may provide users convenience and ease-of-use when donning the exemplary garments. For example, the mitt may be described as providing a more effective and easier way to don a compression garment and as alleviating donning difficulties that may have been associated with prior compression garments. The tightening apparatuses may be used to tighten the exemplary compression garments and portions thereof after the garments have been positioned, or partially donned, about one or more body portions of a user. The tightening apparatuses may be described as efficient and easy-to-use process to tighten and loosening compression garments about a user's body, which may simplify the process of tightening and loosening such compression garments.

One exemplary compression garment may include one or more garment portions wrappable about one or more body portions of a user to apply compression to the one or more body portions. A wraparound garment portion of the one or more garment portions may extend from a proximal end region and may terminate at a distal end region. The distal end region may be configured to be moved by a user to wrap the one or more garment portions about the one or more body portions. The wraparound garment portion may include a mitt at the distal end region defining a mitt opening to receive a hand of a user to assist the user in donning the one or more compression garment portions and in wrapping the one or more garment portions about the one or more body portions of the user. The exemplary compression garment may further include tightening apparatus coupled to the wraparound garment portion to selectively tighten the one or more garment portions about the one or more body portions. The tightening apparatus may selectively adjust a length of the wraparound garment portion defined from the proximal end region to the distal end region.

In one or more embodiments, the one or more garment portions may define a vest garment wrappable about the user's upper torso (e.g., chest, back, stomach, etc.). The vest garment may include a plurality of pressure applying regions to apply pressure to a plurality of upper torso regions of the upper torso of the user when the compression garment is donned to assist in moving lymph from the upper torso to one or more axillary nodes. The wraparound garment portion may be wrappable around at least a portion of the user's upper torso to wrap the one or more garment portions about the user's upper torso, and the tightening apparatus may selectively tighten the one or more garment portions about the user's upper torso. In at least one embodiment, the tightening apparatus may be located on an anterior side of the user when the vest garment is donned by a user.

In one or more embodiments, the one or more garment portions may define a lower torso garment wrappable about the user's lower torso (e.g., waist, pelvis, buttocks, etc.). The lower torso garment may include a plurality of pressure applying regions to apply pressure to a plurality of lower torso regions of the lower torso of the user when the compression garment is donned to assist in moving lymph from the lower torso to one or more axillary nodes. The wraparound garment portion may be wrappable around at least a portion of the user's lower torso to wrap the one or more garment portions about the user's lower torso, and the tightening apparatus may selectively tighten the one or more garment portions about the user's lower torso.

In one or more embodiments, the one or more garment portions may define a leg garment wrappable about a leg of the user. The leg garment may include a plurality of pressure applying regions to apply pressure to a plurality of leg regions of the leg of the user when the compression garment is donned to assist in moving lymph from the leg to one or more axillary nodes. The wraparound garment portion may be wrappable around at least a portion of the user's leg to wrap the one or more garment portions about the user's leg, and the tightening apparatus may selectively tighten the one or more garment portions about the user's leg.

In one or more embodiments, the one or more garment portions may define a head garment wrappable about a head of the user. The head garment may include a plurality of pressure applying regions to apply pressure to a plurality of head regions of the head of the user when the compression garment is donned to assist in moving lymph from the head to one or more axillary nodes. The wraparound garment portion may be wrappable around at least a portion of the user's head to wrap the one or more garment portions about the user's head, and the tightening apparatus may selectively tighten the one or more garment portions about the user's head.

In one or more embodiments, one or more garment portions may include a plurality of cells corresponding to the plurality of pressure applying regions and configured to receive fluid to apply pressure to a plurality of regions of the one or more body portions of the user when the compression garment is donned. Further, the wraparound garment portion may include a plurality of pressure applying regions to apply pressure to a plurality of regions of the one or more body portions of the user to move lymph from the one or more body portions to one or more axillary nodes.

In one or more embodiments, the tightening apparatus may include at least one lace positioned between the proximal end region and the distal end region of the wraparound garment portion and a tightening device coupled to the at least one lace and configured to apply tension on the at least one lace to move the proximal end region relative to the distal end region. Further, the tightening apparatus may further include a plurality of first guide members coupled to the wraparound garment portion and a plurality of second guide members coupled to the wraparound garment portion. The plurality of second guide members may be located closer to the distal end region of the wraparound portion than the plurality of first guide members. The at least one lace may be described as extending back and forth between the plurality of first guide members and the plurality of second guide members. A working length of the at least one lace may be defined by the length of the at least one lace that extends back and forth between the plurality of first guide members and the plurality of second guide members. Further, the working length may be selectively adjustable by using the tightening device to selectively adjust the length of the wraparound garment portion defined from the proximal end region to the distal end region. In at least one embodiment, the tightening device may further include a spool portion rotatable about an axis to store a portion of the at least one lace. In at least one embodiment the tightening device may be configurable in a tightening configuration and a loosening configuration. The working length may be selectively shortenable and restricted from being extended, or lengthened, when the tightening device is configured in the tightening configuration. Also, the working length may be selectively extended, or lengthened, when the tightening device is configured in the loosening configuration.

In one or more embodiments, the mitt opening may be sized to receive more than the fingers of the hand of the user. In one or more embodiments, the distal end region of the wraparound portion may be removably couplable to another garment portion of the one or more garment portions. Further, the distal end region of the wraparound portion may be removably couplable to another garment portion of the one or more garment portions using hook-and-loop fasteners.

One exemplary compression garment system may include a torso garment portion positionable proximate a torso of a body. The torso garment portion may define a plurality of torso pressure applying regions controllable to apply pressure to a plurality of portions of the torso. The torso garment portion may include a left torso garment portion to extend from the posterior of the torso across the left side of the torso to the anterior of the torso and a right torso garment portion to extend from the posterior torso across the right side of the torso to the anterior of the torso. The right torso garment portion may be removably couplable to the left torso garment portion proximate the anterior of the torso, and the right torso garment portion may be removably couplable to the left torso garment portion proximate the posterior of the torso. The torso garment portion may further include a posterior torso garment portion positionable proximate the posterior of the torso and coupled to the left and the right garment portions proximate a neck region of the torso and a left wraparound portion extending from the posterior torso garment portion to extend around the left side of the torso to the anterior of the torso. The left wraparound portion may be removably couplable to at least the left torso garment portion to tighten the torso garment portion about the torso of the body. The torso garment portion may further include a right wraparound portion extending from the posterior torso garment portion to extend around the right side of the torso to the anterior of the torso. The right wraparound portion may be removably couplable to at least the right torso garment portion to tighten the torso garment portion about the torso of the body. One or both of the left and right wraparound portions may include a mitt opening configured to receive a hand of the body to move one or both of the left and right wraparound portion about the torso of the body. Further, one or both of the left and right wraparound portions may include a tightening apparatus to tighten the torso garment portion proximate the body.

In one or more embodiments, the tightening apparatus may include at least one lace positioned between first and second portions of the wraparound portion and a tightening device coupled to the at least one lace and configured to apply tension to the at least one lace to move the first portion of the wraparound portion relative to the second portion of the wraparound portion. Further, in one or more embodiments, the right torso garment portion may be removably couplable to the left torso garment portion proximate the posterior of the torso along a plurality of positions to define a plurality of different sizes for the torso garment portion. Still further, in one or more embodiments, the right torso garment portion may be removably couplable to the left torso garment portion proximate the anterior of the torso using a zipper.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
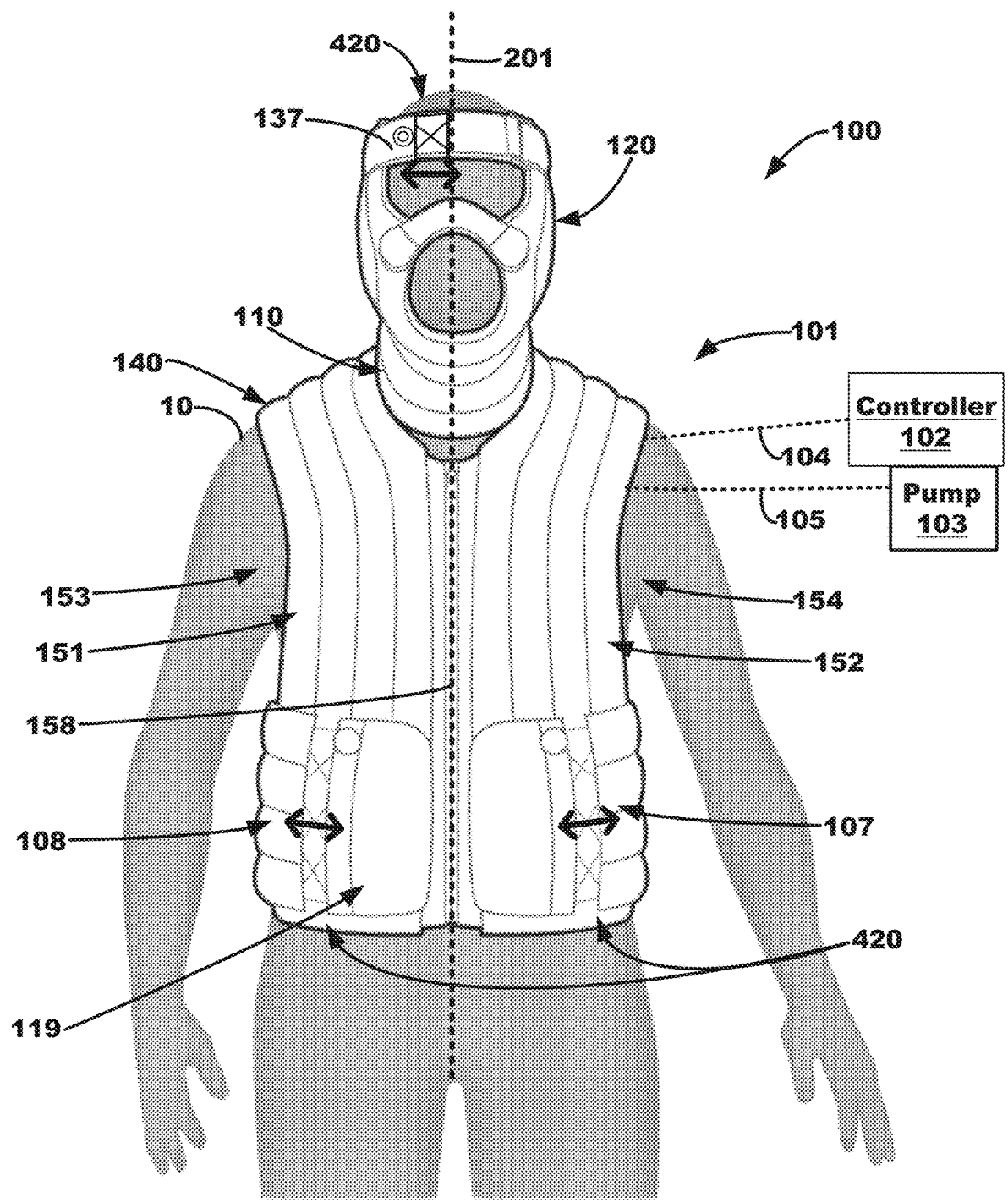
FIG. 1 is a front view of an exemplary compression torso and head garment located on a body.

In the following detailed description of illustrative embodiments, reference is made to the accompanying figures of the drawing, which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary garments, apparatus, systems, and structures shall be described with reference to FIGS. 1-14. It will be apparent to one skilled in the art that elements from one embodiment may be used in combination with elements of the other embodiments, and that the possible embodiments of such garments, apparatus, systems, and structures using combinations of features set forth herein is not limited to the specific embodiments shown in the Figures and/or described herein. Further, it will be recognized that the embodiments described herein may include many elements that are not necessarily shown to scale. Still further, it will be recognized that the size and shape of various elements herein may be modified but still fall within the scope of the present disclosure, although certain one or more shapes and/or sizes, or types of elements, may be advantageous over others.

The present disclosure relates generally to compression garments that include garment portions that are configured to be donned on portions of a body (e.g., person, animal, etc.) and configured to apply pressure to such portions of the body. The compression garments may include one or more mitts for use in assisting users in donning the garments and tightening apparatuses for use in assisting users tighten or loosen the compression garments.

Compression garment systems (e.g., such as compression garments described in U.S. Pat. No. 6,179,796 entitled "Lymphedema treatment system," U.S. Pat. No. 6,645,165 entitled "Lymphedema treatment system," U.S. Pat. No. 6,860,862 entitled "Lymphedema Treatment System," and U.S. Pat. No. 6,966,884 entitled "Lymphedema Treatment System," each of which are herein incorporated by reference in their entireties and which may modify and be modified with features described herein) may be used for various reasons including therapy for people with lymphedema, animals requiring therapy, wound therapy, etc. As used herein, the term body refers to not only humans but any other animal species that may benefit from the concepts and features described herein. These compression garments may be placed around at least a portion of an individual's body and used to apply pressure to the body at an affected extremity (e.g., head, neck, arm, torso, a shoulder, etc.). Some embodiments described herein may include a compression system having a garment configured to be positioned on (e.g., wrapped around, placed adjacent, located in proximity to, etc.) at least a portion of a body (e.g., human body, arm, torso, a shoulder, head, neck, etc.). The compression garments may be donned (e.g., put on) and doffed (e.g., taken off) by individuals themselves or with help from others. The garment may also include one or more chambers (e.g., cells, compartments, sealed volumes, bladders etc.) distributed (e.g., distributed throughout, distributed in concentric patterns "radiating" away from a central point or axis, along a length, etc.) of the garment configured to receive a fluid (e.g., air) to perform compression therapy.

The compression therapy provided by the compression garment systems may help to treat lymphedema. Lymphedema is a condition of localized fluid retention and tissue swelling that may be inherited, caused by cancer treatments, caused by parasitic infections, injury, surgery, etc. For example, lymphedema of the head and neck may cause swelling around the head, neck, submandibular area, cheek, nose, eyelids, etc. Compression garments described herein covering the head and neck may be used by an affected individual to provide a therapeutic benefit. Specifically, the compression garments may be configured to manipulate lymph nodes or vessels by applying pressure to move lymph toward more beneficial locations (e.g., toward drainage areas, away from affected regions, etc.). For example, compression therapy using the systems described herein may be performed around the head and neck area to help treat lymphedema in the head and neck area by, e.g., moving lymph towards the torso.

The compression garments described herein may be configured to apply pressure to the affected regions of the body to apply compression therapy. The compression garments may include various portions that each includes controllable pressure applying regions. Each controllable pressure applying region may be configured to apply pressure to a specific portion of the body (e.g., at a specific time during therapy). The controllable pressure applying regions may work in combination with one another to help provide therapy by applying a sequence of pressures on the body that moves lymph in a desired direction (e.g., from the head towards the neck, from the neck towards the torso, etc.). Such application of a sequence of pressures on the body that moves lymph (e.g., pressure being applied to one or more portions of the head and neck, at different times during a compression therapy period) may be referred to as applying dynamic pressure to the body. The sequence of pressures may be referred to as a pressure gradients, e.g., from a distal region to a proximal region. Additionally, in some embodiments, dynamic pressure may not be applied sequentially, and instead, be applied non-sequentially.

The controllable pressure applying regions of the compression garments may also apply static pressure to the body. For example, the compression garments may apply a constant pressure when a portion of the garment is positioned on, or about, the body over a therapy time period (e.g., static pressure over the therapy time period) or may apply a pressure that may be controlled to change over time during the therapy time period (e.g., dynamic pressure). In one or more embodiments, the dynamic pressure may be applied to the portion of the body through one or more chambers in the compression garment. The one or more chambers may be configured to receive fluid. Alternately, or in combination with one or more fluid receiving chambers, such pressures may be applied using one or more actuatable elements in the compression garment configured to apply pressure to the body (e.g., electrically controlled materials suitable to provide compression).

Figure 2:
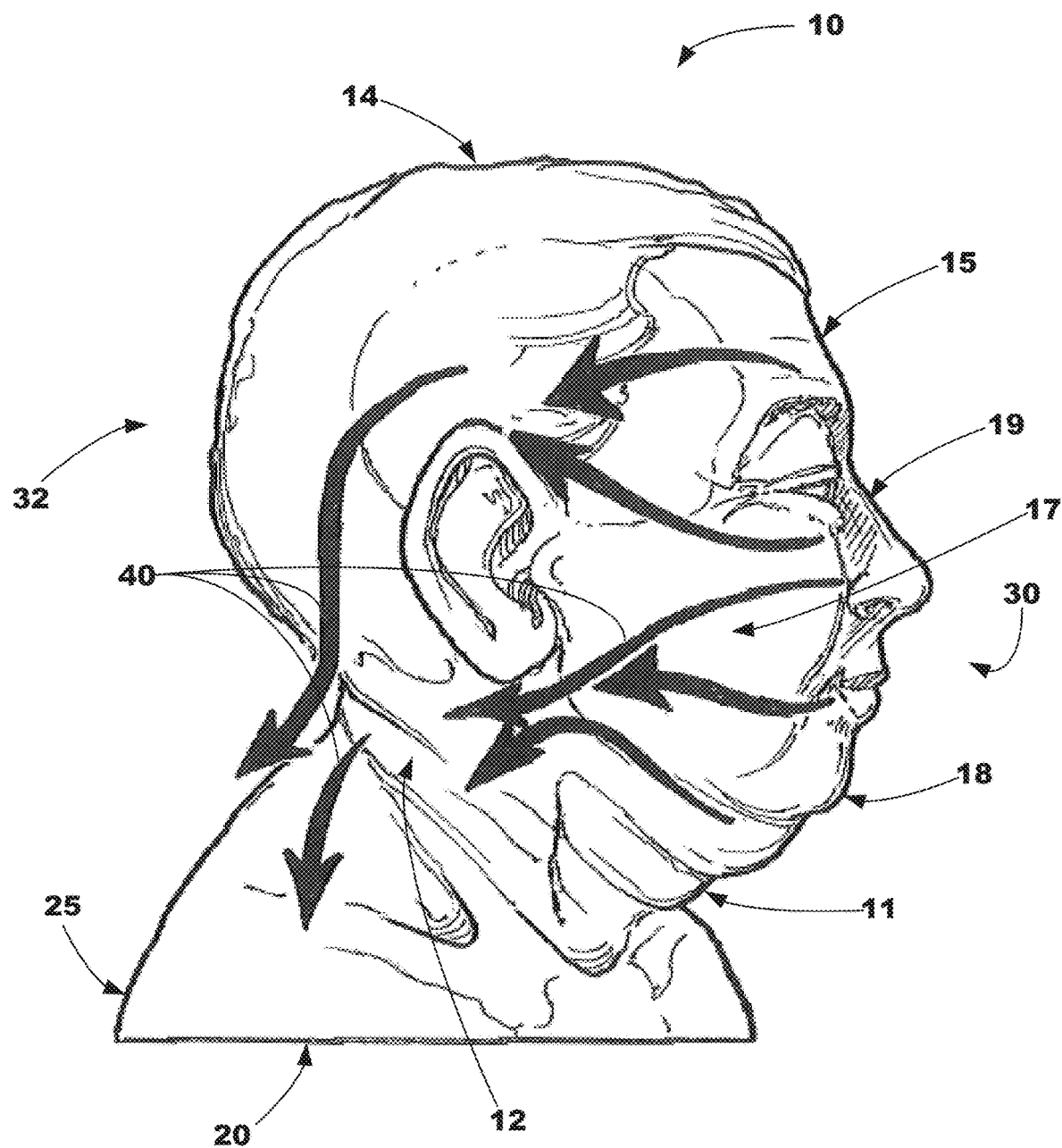
FIG. 2 is an exemplary side view of a head and a neck of a human body illustrating the directional flow of lymph through the head and neck using the exemplary compression system.
Figure 3:
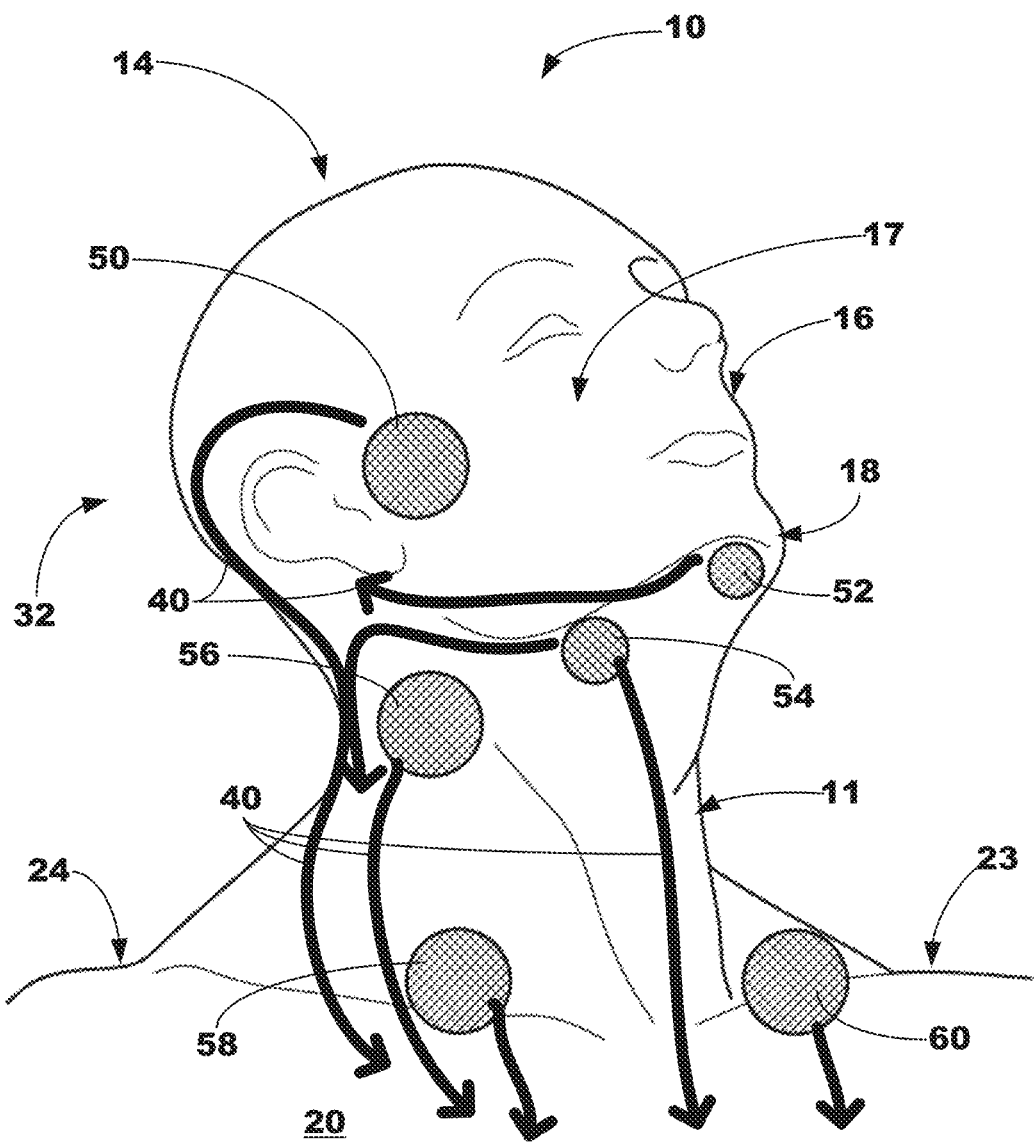
FIG. 3 is a perspective view of a head and a neck of a human body illustrating specific lymph nodes and the directional flow of lymph through the head and neck using the exemplary compression system.
Figure 4:
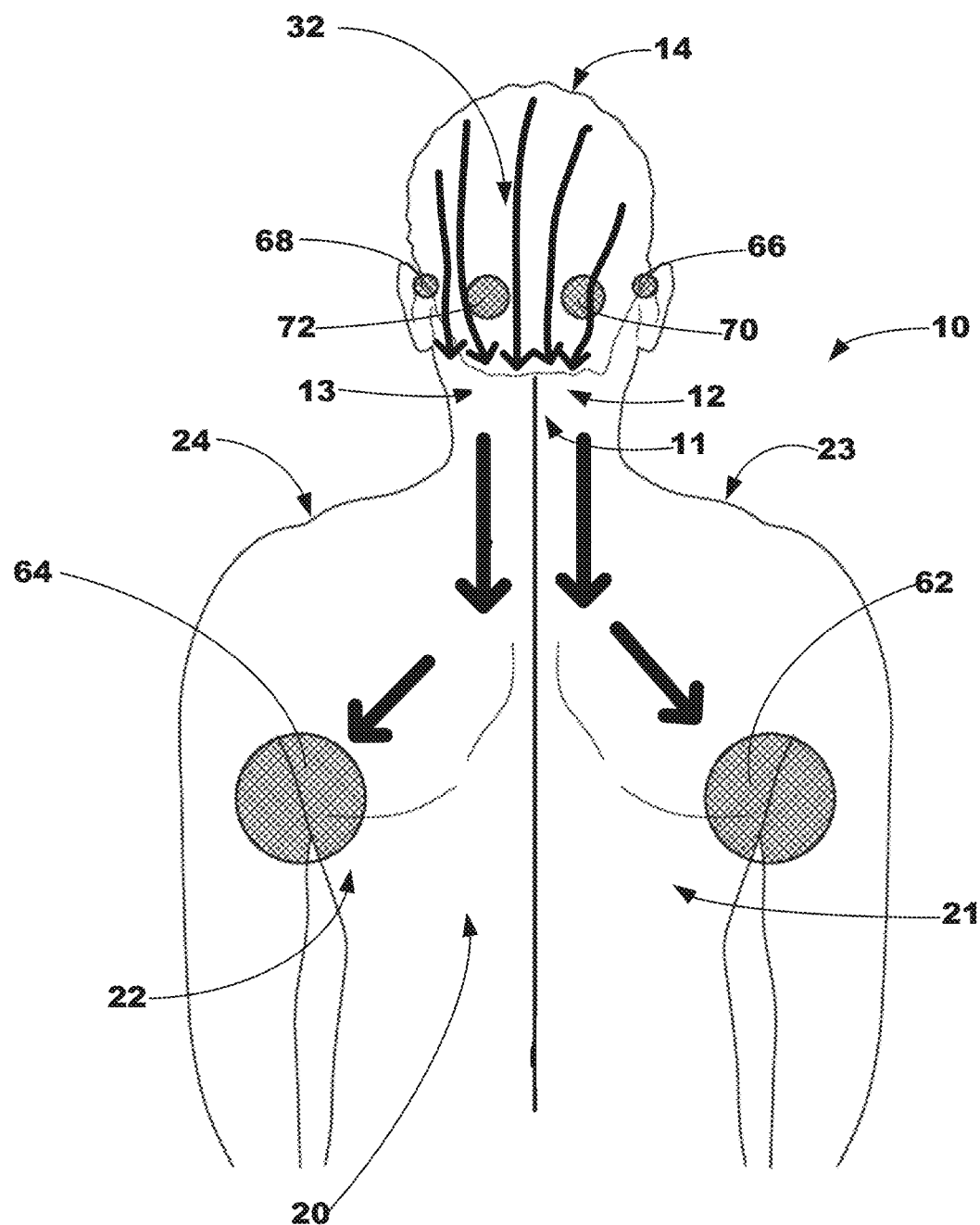
FIG. 4 is an exemplary back view of a human body illustrating specific lymph nodes and the directional flow of lymph through the body using the exemplary compression system.

Exemplary compression garments may include one or more, or a plurality, of garment portions wrappable about one or more body portions of a user to, e.g., apply compression to the one or more body portions. An exemplary compression garment system 100 including a garment 101 (e.g., compression garment) configured to be positioned around, or about, one or more portions of a body, e.g., a human body 10, such as the head, the neck, and the torso is shown in FIG. 1. The garment 101 may be positioned relative to the body in a variety of different ways (e.g., relative to a head 14, a neck 11, an anterior portion of the body 10, a posterior portion of the body 10, a forehead 15, a chin 18, a right and left cheek 16, 17, a torso 20 as shown in FIGS. 2-4). For example, as shown in FIG. 1, the garment 101 is positioned around the head, neck, and torso of the body 10. In one or more embodiments, the garment 101 may also cover the arms, waist, legs, or any other portion of the body 10. Although as shown in FIG. 1 the garment 101 is positioned on the head, neck, and torso of the body 10, the garment 101 may include only portions positioned on the head and neck of the body 10, only portions positioned on the head of the body 10, only portions positioned on the torso of the body 10, and only portions positioned on the torso and heck of the body 10.

The exemplary garment 101 may include a neck garment portion 110, a head garment portion 120, and a torso garment portion 140. Each of the neck garment portion 110, the head garment portion 120, and the torso garment portion 140 may be coupled to each other in various ways. For example, in one or more embodiments, the head garment portion 120 and the neck garment portion 110 may be coupled to one another. More specifically, the head garment portion 120 and the neck garment portion 110 may be coupled to one another at the posterior of the body 10, the anterior of the body 10, along the portion in which the head and neck garment portions 120, 110 intersect, etc.

The torso garment portion 140 may be configured to be positioned proximate the torso of the body 10. In one or more embodiments, the torso garment portion 140 may be couplable to the neck garment portion 110 (e.g., the torso garment portion 140 may be separate from the head garment portion 120 and neck garment portion 110, the torso garment portion 140 may be removably coupled to the neck garment portion 110 and/or the head garment portion 120, for example, using hook and loop fasteners, etc.). For example, the torso garment portion 140 and the neck garment portion 110 may be coupled to one another at the posterior of the body 10, the anterior of the body 10, along the portion in which the torso garment portion 140 and neck garment portion 110 intersect, etc. Still further, in one or more embodiments, the torso garment portion 140 and the neck garment portion 110 may be coupled to one another along the entire portion in which the torso garment portion 140 and neck garment portions 110 intersect (e.g., where such portions lie next to one another) or only along portions thereof (e.g., leaving openings at the coupling region for the garment to flex and adapt to the body of the user).

Figure 7:
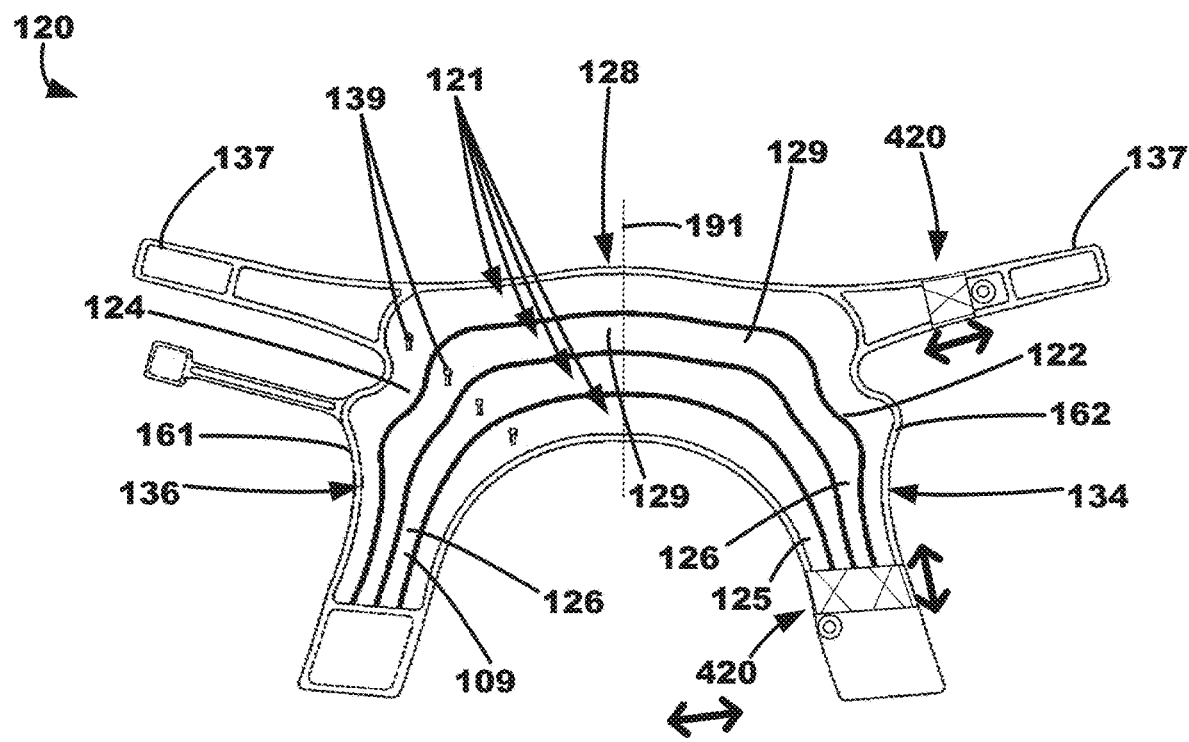
FIG. 7 is a plan view of a head garment portion of an exemplary compression garment such as shown in FIG. 1 including one or more pressure applying regions.
Figure 8:
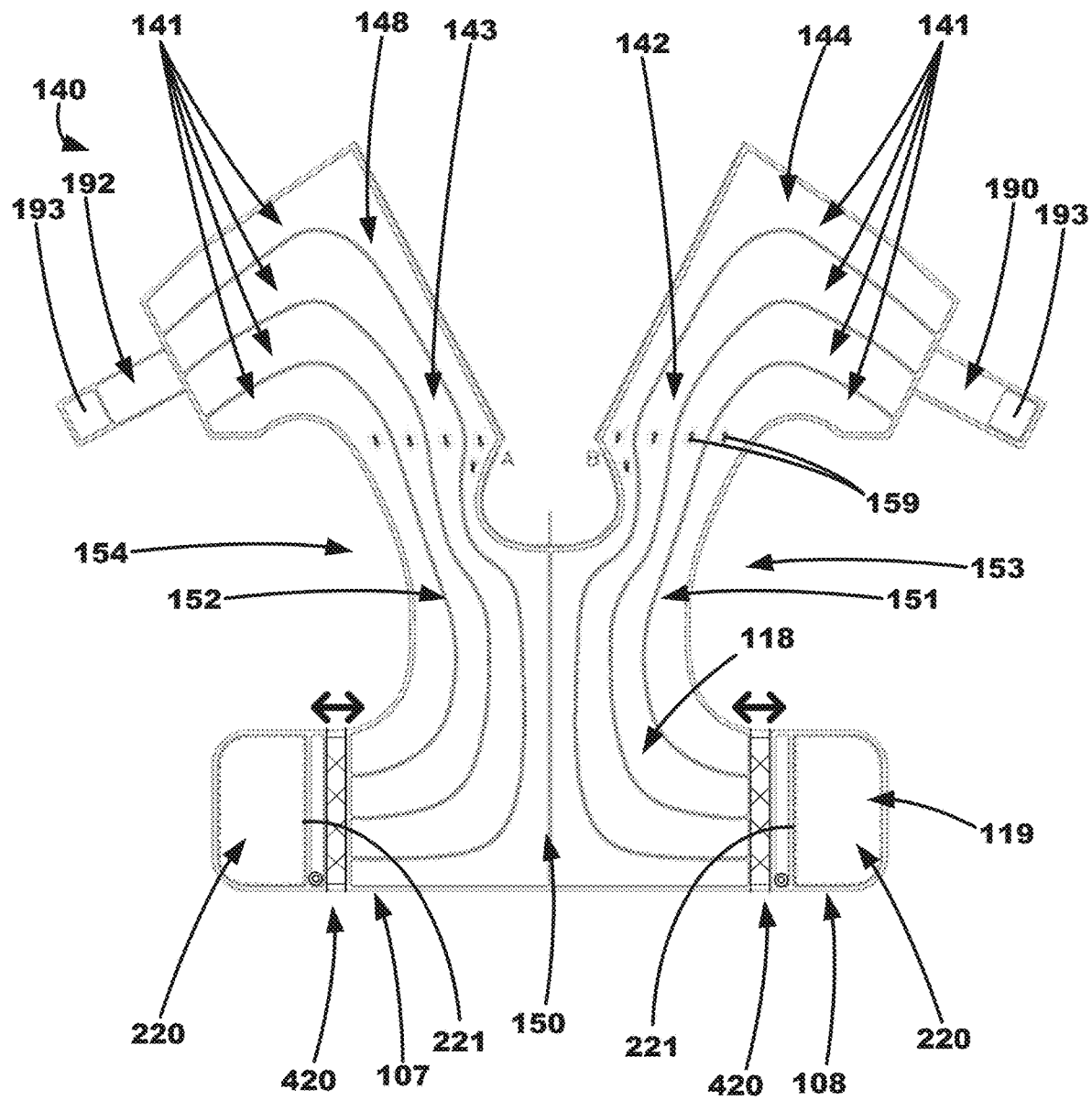
FIG. 8 is a plan view of a torso garment portion and a neck garment portion of an exemplary compression garment system such as shown in FIG. 1 including one or more pressure applying regions.

The garment 101 may define, or include, pressure applying regions (e.g., as shown in FIGS. 7-8) located at regions of the garment 101. Each of the pressure applying regions may be controllable or configurable to apply pressure to a portion of the body. For example, the head garment portion 120 may include head pressure applying regions that are controllable or configurable to apply pressure to one or more portions of the head (e.g., to the forehead, cheeks, under the chin, posterior head), the neck garment portion 110 may include neck pressure applying regions that are controllable or configurable to apply pressure to one or more portions of the neck (e.g., posterior neck regions, side neck regions, etc.), and the torso garment portion 140 may include torso pressure applying regions controllable or configurable to apply pressure to one or more portions of the torso (e.g., torso regions under each arm, the anterior torso, the posterior torso, etc.). In one or more embodiments, the garment 101 may include an exterior material covering the pressure applying regions.

The head garment portion 120 may be configured to be donned on the head of the body 10. In other words, the head garment portion 120 may be positioned on and secured to the head of the body 10 (e.g., secured using fasteners across the nose, fasteners across the forehead, fasteners under the chin, fasteners over the top of the head, etc.). For example, such fastening apparatus may allow one garment to be adjusted for use with different size and shaped body parts. In one or more embodiments, the head garment portion 120 may be described as configured to be positioned around both sides of the head of the body 10 from the posterior of the head to the anterior of the head.

As shown in the plan view of the head garment portion 120 in FIG. 7, the head garment portion 120 may include a posterior head garment portion 128, a right head garment portion 134, and a left head garment portion 136. The posterior head garment portion 128 may be positionable proximate a posterior of the head of the body 10. The right head garment portion 134 may extend from the posterior head garment portion 128 and be positionable on (e.g., wrapped around) a right side of the head from the posterior of the head to an anterior of the head. The left head garment portion 136 may extend from the posterior head garment portion 128 and be positionable on (e.g., wrapped around) a left side of the head from the posterior of the head to the anterior of the head. The posterior head garment portion 128, the right head garment portion 134, and the left head garment portion 136 (or each of such portions) may include pressure applying regions (e.g., each of the one or more head pressure applying regions for applying compression on regions of the body associated with each of such portions, one or more head pressure applying regions for applying compression on, or to, one or more regions of the body corresponding to one or more portions of the garment, etc.) that are configurable or controllable to apply pressure to the posterior of the head, the right side of the head, and the left side of the head, respectively.

The head garment portion 120 may also include a right cheek garment portion 122 and a left cheek garment portion 124. The right cheek garment portion 122 may be positionable proximate a right cheek of the head and the left cheek garment portion 124 may be positionable proximate a left cheek of the head. Each of the right and left cheek garment portions 122, 124 may include pressure applying regions (e.g., one or more cheek pressure applying regions) that may be configurable or controllable to apply pressure to a portion of cheek. The head garment portion 120 may also include a right under-chin portion 125 and a left under-chin portion 109 defining an under-chin garment portion. The under-chin garment portion may include pressure applying regions (e.g., one or more under chin pressure applying regions) that may be configurable to apply pressure to a portion under the chin (e.g., at the "waddle" area).

The head garment portion 120 may be donned on the head of the body in a variety of different ways. For example, portions of the head garment portion 120 may be attached to other portions of the head garment portion 120 using a variety of different wraparound portions, or straps, and/or one or more connection elements. Any suitable connection apparatus may be used for donning the head garment portion 120 or any other garment portion described herein, such as flexible or rigid connection elements, hook and loop fasteners, straps connected to the garment, additional or separate connection garment elements or straps, mating hooks, elements shaped to form to a body part (such as the bridge of the nose), etc.

These wraparound portions, or straps, and connection elements may maintain, or keep, portions of the head garment portion 120 (e.g., surfaces associated with pressure applying regions) close to the surface of body such that the head garment portion 120 may effectively apply pressure to a particular portion of the body (e.g., the cheeks, under the chin, forehead, temples), such as, for example, when fluid is provided to chambers of pressure applying regions. In other words, the wraparound portions and/or connection elements may assist in preventing the head garment portion 120 from moving away from the surface of portion of the body when pressure is being applied using pressure applying regions (e.g., such as when fluid is provided to chambers of pressure applying regions) and instead, e.g., stay near the portion of the body such that pressure may be effectively applied to the portion of the body. The different wraparound portions and/or connection elements keep the garment portions from moving away from the body as pressure is being applied such that even pressure applying regions (e.g., to apply pressure evenly) at edges of the garment are maintained in position during application of pressure to body regions adjacent such edges (e.g., garment edges proximate the cheeks of the head, garment edges near the chin of the head, garment edges near under the chin, garment edges near the temples of the head, etc.).

For example, the head garment portion 120 may include the under-chin garment portion including a right wraparound under-chin portion 125, a left wraparound under-chin portion 109, and a wraparound forehead strap 137, each of which may act as restraints, straps, or connection elements to keep the head garment portion 120 in place or position. The right wraparound under-chin garment portion 125 may include one or more under chin connection elements configured to connect the right cheek garment portion 122 and the left cheek garment portion 124. As shown in FIG. 7, the right wraparound under-chin portion 125 may further include tightening apparatus 420 to selectively adjust, or vary, a length of the right wraparound under-chin portion 125 as indicated by the double-sided arrow, which will be described further herein with respect to FIGS. 5 and 13.

The wraparound forehead strap 137 may be positionable proximate a forehead of the head. The wraparound forehead strap 137 may include one or more forehead connection elements that may be configured for use in donning the head garment portion 120 on the head. In other words, the one or more forehead connection elements may pull one portion of the head garment portion 120 closer to another portion of the head garment portion 120 to position (e.g., secure) the head garment portion 120 on the head of the body. As shown in FIGS. 1 and 7, the wraparound forehead strap 137 may further include tightening apparatus 420 to selectively adjust, or vary, a length of the wraparound forehead strap 137 as indicated by the double-sided arrow, which will be described further herein with respect to FIGS. 5 and 13.

One will recognize that any number of wraparound portions and/or connection elements may be used to connect different portions of the head garment such that the pressure applying regions thereof are properly positioned adjacent desired regions of the head and maintained in positioned as pressure is being applied either dynamically or statically. Further, one will recognize that one or more wraparound portions may be integral or separate from one another and/or the remainder of the garment.

The neck garment portion 110 may be configured to be donned on a neck of the body 10. In one or more embodiments, the neck garment portion 110 may be described as configured to be positioned around both sides of the neck from the posterior of the neck to the anterior of the neck.

The torso garment portion 140 may be described as configured to be positioned around both sides of the torso from the posterior of the torso to the anterior of the torso of the body 10. The torso garment portion 140 may include pressure applying regions (e.g., one or more torso pressure applying regions) configurable or controllable to apply pressure to one or more portions of the torso. In one or more embodiments, the torso garment portion 140 may be coupled to the neck garment portion 110 and/or the head garment portion 120. Further, in one or more embodiments, the neck garment portion 110 may be coupled between at least a portion of the head garment portion 120 and at least a portion of the torso garment portion 140. In yet other embodiments, the torso garment portion 140 may not be coupled to either the head garment portion 120 or the neck garment portion 110.

The torso garment portion 140 may include a posterior torso garment portion 150, a right torso garment portion 151, and a left torso garment portion 152. The posterior torso garment portion 150 may be positionable proximate a posterior of the torso of the body, the right torso garment portion 151 may extend from the posterior torso garment portion 150 and be positionable to the anterior of the torso, and the left torso garment portion 152 may extend from the posterior torso garment portion 150 and be positionable to the anterior of the torso. In one or more embodiments, the right torso garment portion 151 may define a right arm opening 153 proximate a right arm of the body such that the right arm may extend outward from the garment 101 and the left torso garment portion 152 may define a left arm opening 154 proximate a left arm of the body such that the left arm may extend outward from the garment 101.

The right and left torso garment portions 151, 152 may be coupled to each other after donning the torso garment portion 140 on the torso of the body to attach (e.g., secure) the torso garment portion 140 to the torso. The right torso garment portion 151 may be coupled to the left torso garment portion 152 in any suitable manner. For example, the right and/or left torso garment portions 151, 152 may include fastening apparatus to, e.g., fasten or couple a region of the right torso garment portion 151 to a portion of the left torso garment portion 152. Although the right torso garment portion 151 is coupled to the left torso garment portion 152 using a zipper 158 as shown, any fastening apparatus may be used such as, e.g., hook and loop fasteners, draw strings, buttons, etc.

Additionally, the torso garment portion 140 may further include a left wraparound portion 107 and a right wraparound portion 108, which may be configured to further couple, or secure, the torso garment portion 140 about the torso of the body 10. More specifically, it may be described that the left and right wraparound portions 107, 108 may be configured to done, or wrap, and "tighten" the torso garment portion 140 about the torso of the body 10, which may be described further herein with respect to FIGS. 9-11. Each of, the left and right wraparound portions 107, 108 may further include tightening apparatus 420 that may be used for to further tighten or loosen the torso garment portion 140 about the torso of the body 10, which will be described further herein with respect to FIGS. 5 and 13. The tightening apparatus 420 may be used to selectively adjust, or vary, a length of the wraparound portions 107, 108 as indicated by the double-sided arrows, which will be described further herein with respect to FIGS. 5 and 13.

As shown in FIG. 1, the compression garment system 100 may also include a controller 102 or control apparatus configured to control the pressure applied to the portion of the body by each of the pressure applying regions of the garment 101. For example, the controller 102 may control the pressure applied to the portion of the body by each of the pressure applying regions independent from one another or at the same time. Further, for example, the pressure applying regions may be controlled in groups or combinations. In one or more embodiments, the controller 102 may be configured to control the pressure applying regions in a variety of different sequences (e.g., applying pressure in a predetermined manner) that may be, e.g., suitable for carrying out lymphedema therapy.

Figure 14:
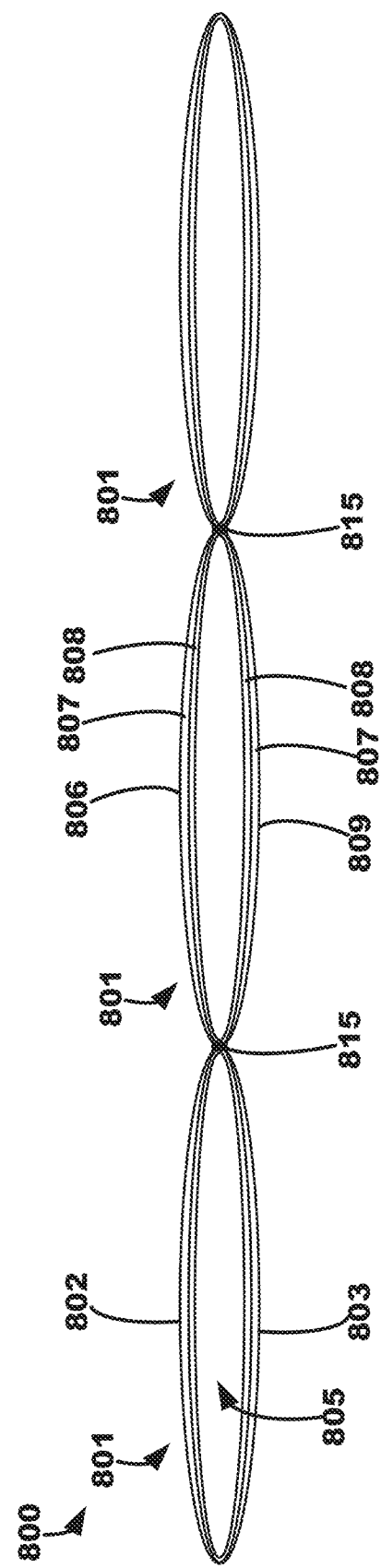
FIG. 14 is a cross-sectional view of one or more cells including actuatable elements (e.g., inflatable chambers or cells) of an exemplary compression garment that may be used with one of the exemplary garment portions such as shown in FIGS. 1 and 5-12.

Also as shown in FIG. 1, the compression garment system 100 may include a pump 103 that may be controlled by the controller 102 to provide a fluid to/from the one or more chambers (e.g., one or more chambers 806 as shown in FIG. 14) of each of the pressure applying regions, e.g., a fluid such as a liquid or gas in the chambers, so as to apply a compression therapy when the compression garment 101 includes one or more fluid filled chambers. For example, the pump 103 may be connected to one or more of the plurality of chambers corresponding to the plurality of pressure applying regions by a plurality of lines or tubing 105 so as to provide flow of fluid thereto or removal of fluid therefrom.

Further, in one or more embodiments, as shown in FIG. 1, the controller 102 may be connected to one or more components of the compression garment system via one or more electrical lines and/or wirelessly, as represented generally by dashed lines 104. For example, controller 102 may be connected to communicate and control the pressure applying regions (e.g., such as electrically actuatable pressure applying regions of the garment configured to apply pressure to the body) either with use of physical electrical connections and/or wirelessly.

The controllable pressure applying regions of the garment 101 under control of controller 102 allows the system 100 to provide compression therapy to an individual (e.g., a patient) wearing the garment 101 such that lymph flows throughout the body 10 in desired directions, e.g., such as directions 40 as shown in FIGS. 2-4. In other words, by controlling the pressure applying regions in a variety of different sequences (e.g., applying pressure in a predetermined manner), for example, lymph may flow generally from the head 14 of the body 10 towards the neck 11 of the body 10. For example, the lymph may be controlled to flow from an anterior 30 of the head 14 towards a posterior 32 of the head 14 and downwards towards the neck 11. Specifically, for example, the lymph may flow from the forehead 15, the nasal bridge 19, and under the chin 18 towards the right cheek 17 and downwards towards the neck 11 (e.g., right side of neck 12) and the posterior 25 of the torso 20. This direction 40 of lymph may provide relief to an individual by moving excess lymph from the head 14, and ultimately, moving such lymph towards the torso 20 (e.g., trunk, shoulders, chest, back, waist, etc.).

The various nodes located in the head 14 and neck 11 of the body 10 are shown in FIG. 3. For example, the submental lymph nodes 52 are located the under chin 18 of the head 14 and the parotid lymph nodes 50 are located proximate the right cheek 17 and the left cheek 16 (parotid lymph nodes of left cheek 16 not shown in FIG. 3). The accumulation of lymph may occur near the parotid lymph nodes 50 and the submental lymph nodes 52 and may be pushed during compression therapy by the compression garment donned on the body 10 towards the posterior 32 of the head 14 as illustrated by directional arrows 40 (e.g., by controlling the pressure applying regions proximate at least the cheeks and under the chin in a predetermined manner). With continued compression therapy (e.g., by controlling the pressure applying regions proximate at least the sides of the head and the posterior of the head), the lymph then moves towards the submandibular lymph nodes 54 and superficial and deep cervical lymph nodes 56 located proximate the neck 11. The compression therapy is then configured (e.g., by controlling the pressure applying regions proximate at least the neck in a predetermined manner) to move lymph towards the right infra and supra clavicular lymph nodes 58 and the left infra and supra clavicular lymph nodes 60, which are located at the base of the neck 11 and proximate the right shoulder 24 and the left shoulder 23, respectively, and downwards towards the torso 20.

Various nodes located in the posterior 32 of the head 14 and the torso 20 are shown in FIG. 4. During compression therapy using a compression garment (e.g., by controlling the pressure applying regions of the head garment 120 and neck garment 110 in a predetermined manner), lymph may travel downward along the posterior 32 of the body 10 from the head 14 towards the torso 20. For example, lymph may travel from the top of the head 14 towards the right retroauricular lymph nodes 66 and the right occipital lymph nodes 70 located proximate the right side 12 of the neck 11 and towards the left retroauricular lymph nodes 68 and the left occipital lymph nodes 72 located proximate the left side 13 of the neck 11. The compression therapy (e.g., by controlling the pressure applying regions of the garment 101 in a predetermined manner) may then move the lymph further downwards from the head 14 and past the right and left shoulders 23, 24 and towards the torso 20. Specifically, the lymph may move towards the right axillary nodes 62 located proximate the right under arm region 21 and the left axillary nodes 64 located proximate the left under arm region 22.

Figure 5:
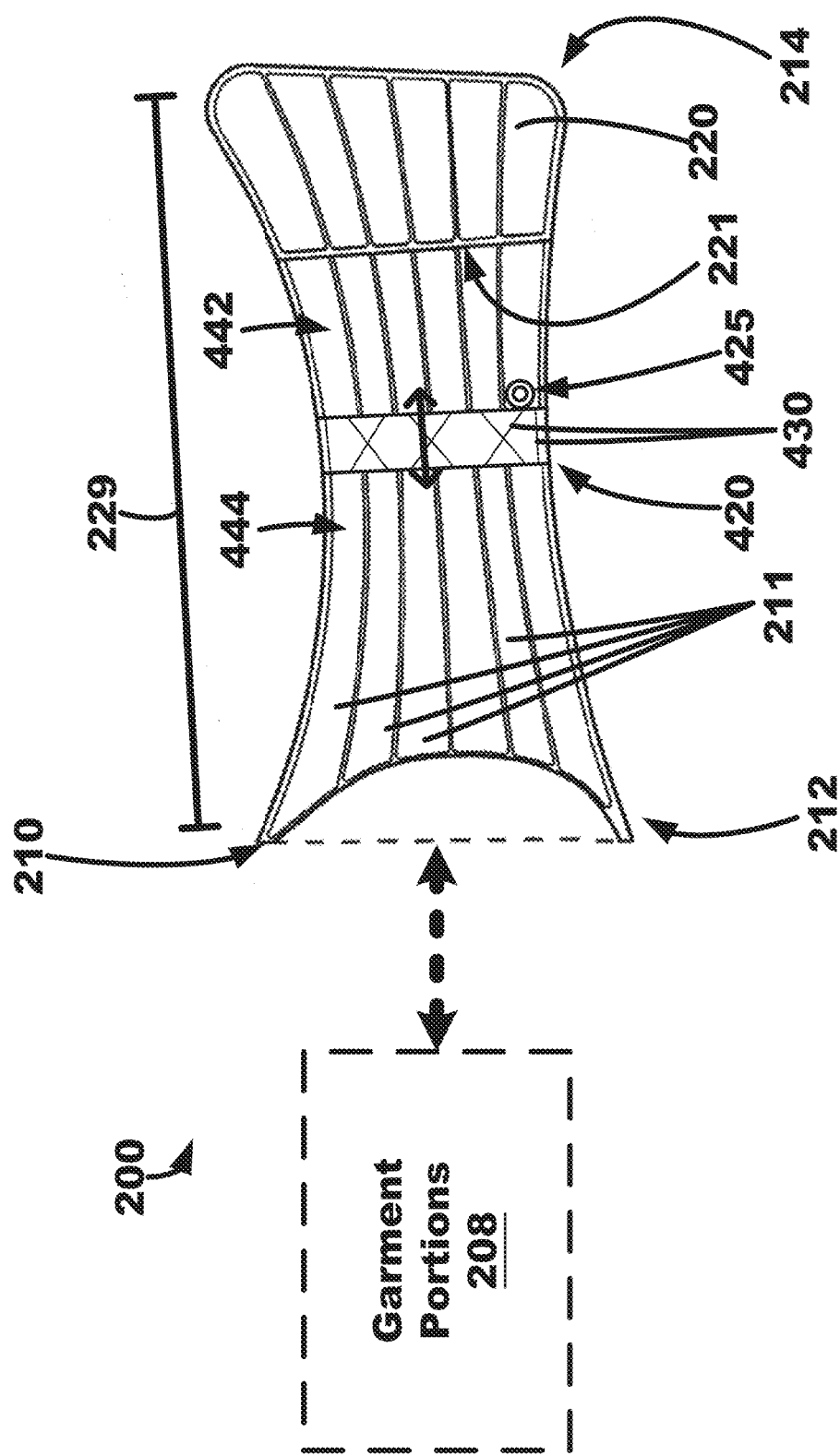
FIG. 5 is a diagrammatic view of an exemplary compression garment including a wraparound portion having a mitt and tightening apparatus.

The torso garment portion 101, the head garment portion 110, and the head garment portion 120 of FIG. 1 are a few examples of compression garments, or garment portions, that may use, or include, the exemplary mitts and tightening apparatuses described herein. It is be understood that the exemplary mitts and tightening apparatuses described herein may be used with one or more, or a plurality of, various compression garments and/or garment portions as described herein with respect to the diagrammatic view of an exemplary compression garment 200 as shown in FIG. 5. The exemplary garment 200 may include a wraparound portion 210 and one or more additional garment portions 208 (diagrammatically represented by a dashed-line box). In this embodiment, the garment 200 may be described as including a single portion that may extend around, or about, one or more body portions a user (e.g., a torso, a lower torso portion, an upper torso portion, a buttock, a pelvis portion, a leg, a trunk, an arm, a head, a neck, etc.), which is the wraparound portion 210. Although a single wraparound portion 210 is depicted in FIG. 5, it is to be understood that the exemplary embodiments described herein may include more than one wraparound portion such as, e.g., a plurality of wraparound portions that each extends around, or about, one or more body portions of a user. The one or more additional garment portions 208 may be coupled to the wraparound portion 210 as indicated by the double-sided dashed arrow. The one or more additional garment portions 208 may include an arm portion configured to be placed about a user's arm, an upper torso portion configured to be placed about a user's upper torso, a lower torso portion configured to be placed about a user's lower torso, a leg portion configured to be placed about a user's leg, a head portion configured to be placed about a user's head, etc.

The wraparound portion 210 may extend from a proximal end region 212 to a distal end region 214. The wraparound portion 210 may be described as extending from the proximal end region 212 and terminating at the distal end region 214. In other words, the wraparound portion 210 may not extend beyond, or past, the distal end region 214. The proximal end region 212 may be configured to be coupled to the one or more additional garment portions 208 such as, e.g., various torso garment portions. In one or more embodiments, the proximal end region 212 may be fixedly coupled to the one or more additional garment portions 208, e.g., through stitching, welding, adhesive, etc. In one or more other embodiments, the proximal end region 212 may be removably coupled to the one or more additional garment portions 208, e.g., through hook-and-loop fasteners, etc. In one or more embodiments, the wraparound portion 210, or regions or parts thereof, may be integral with the one or more additional garment portions 208.

For example, the right wraparound portion 108 of the torso garment 140 may extend from a proximal end region 118 to a distal end region 119 as shown in FIGS. 1 and 8. The proximal end region 118 may be coupled to other portions or regions of the torso garment 140 such as the posterior torso garment portion 150, the right torso garment portion 151, and the left torso garment portion 152. As shown, the proximal end region 118 of the right wraparound portion 108 may be described as being integral with, or flowing from, the other portions or regions of the torso garment 140. Further, the right wraparound portion 108 extends from the other portions or regions of the torso garment 140 and terminates at a distal end region 119, which includes a mitt as will be further described herein.

The wraparound portion 210 may be generally described as being configured to be wrapped around, or about, one or more body portions, or parts, a user to, e.g., secure or couple the exemplary garment 200 to or about the user's body. Further, it may be described that the wraparound portion 210 is configured to complete a circle or revolution around the one or more body portions such that at least a portion including the wraparound portion 210 of the garment 200 extends at least partially around the one or more body portions. In some embodiments, the wraparound portion 210 may work in conjunction with the other garment portions 208 to complete a circle or revolution around the one or more body portions such that at least a portion including the wraparound portion 210 of the garment 200 extends at least partially around the one or more body portions. Still further, the wraparound portion 210 may be configured to tighten one or more portions of the garment 200 about the one or more body portions of the user and position, or locate, the remaining garment portions about the user's body.

The wraparound portion 210 may include one or more pressure applying regions 211 as shown in FIG. 5, which may be controlled by the controller 102 and pump 103 as described herein with respect to FIG. 1. In other embodiments, the wraparound portion 210 may not include pressure applying regions, and instead, may solely provide the functionality of securing the one or more additional garment portions 208, which may include one or more pressure applying regions.

The wraparound portion 210 may include a mitt 220 located at, or proximate to, the distal end region 214. The mitt 220 may define, or include, a mitt opening 221 that is configured, or designed, to receive a hand of a user to assist the user in donning the garment 200 as will be described further herein with respect to FIGS. 10-11. In one or more embodiments, the mitt opening 221 may be defined by three closed sides and one open side. In other words, the mitt 220 may form a pocket, which may be referred to as the mitt opening 221. Further, in one or embodiments such as shown in the figures, a closed side of the mitt opening 221 may terminate the distal end region 214 of the wraparound portion 210. In the embodiment depicted in the figures, a first portion of the mitt 220 may be part of the distal end region 214 of the wraparound portion 210 and a second portion of the mitt 220 may be attached, or coupled, (e.g., stitched, adhered, etc.) to the distal end region 214 of the wraparound portion 110 to create, or provide, the mitt 220 and mitt opening 221 (e.g., attached on three sides to provide one open side). It is to be understood that the mitt 220 and mitt opening 221, or pocket, may be formed in any manner. For example, the mitt 220, and thus, the mitt opening 221, may be created, or formed, by folding a portion of the wraparound portion 210 back onto itself and coupling the top and bottom edges to form a pocket, which is the mitt opening 221.

Figure 6:
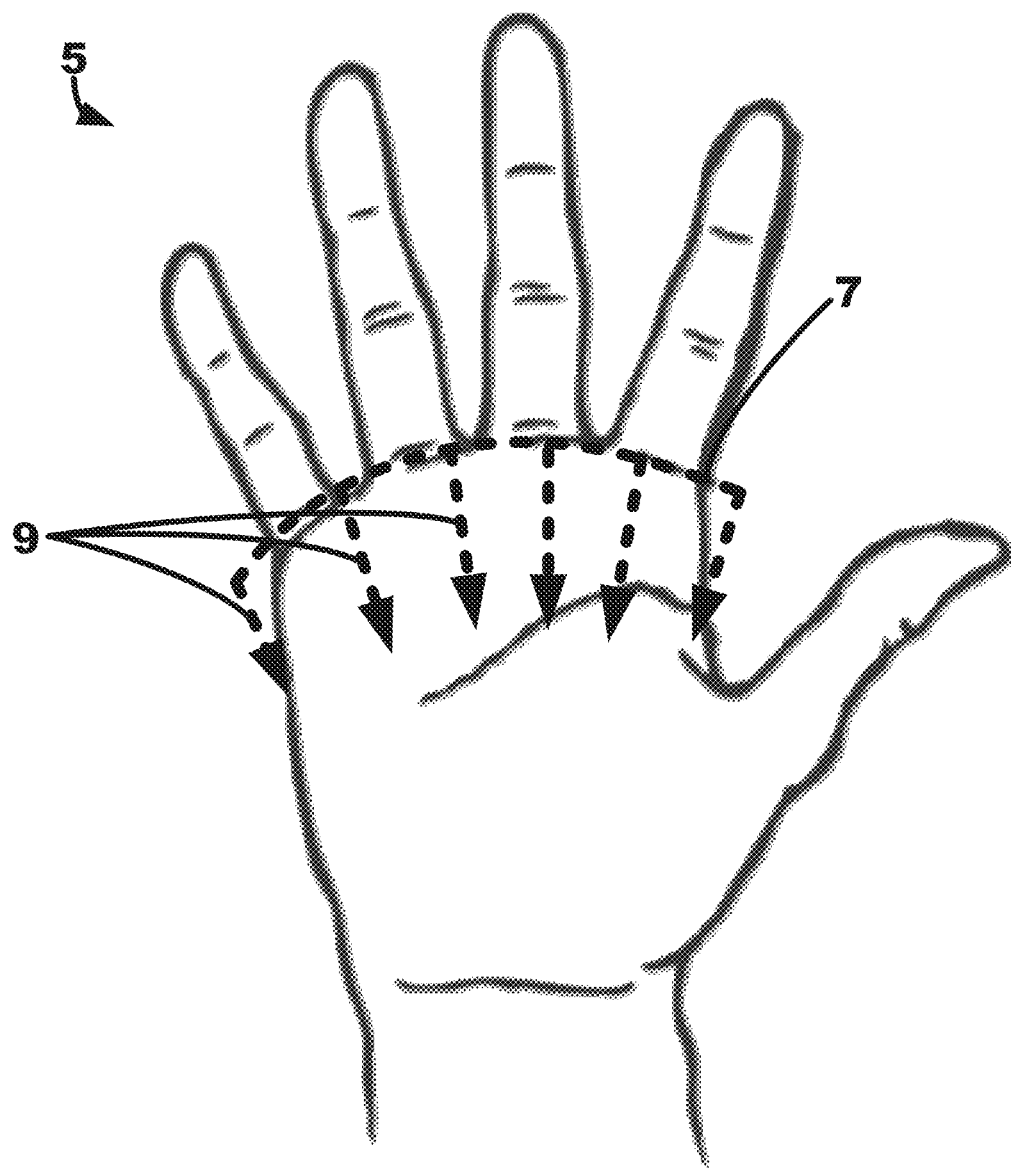
FIG. 6 is a diagram of a hand for use in describing the mitts of FIGS. 1 and 5.

The mitt 220 as well the mitt opening 221 may be sized and constructed such that the mitt opening 221 is configured to receive more than the fingers, or a portion of the fingers, of a user's hand. In other words, the mitt opening 221 may define a pocket that is larger than a typical-human user's fingers so as to receive a typical human-user's hand or at least a majority of the user's hand. Further, the mitt opening 221 may be described in terms of a user's metacarpophalangeal joints (e.g., the joints between the phalangeal and metacarpal bones) as shown in FIG. 6. For example, the mitt opening 221 may be configured in size to receive, or hold, the index finger, the middle finger, the ring finger, the pinky, and at least a portion, or region, of a user's hand 5 beyond the metacarpophalangeal joint line 7 as indicated by the arrows 9. Still further, the mitt 220 may be configured such that the mitt opening 221 opens in a direction toward the hand which the mitt 220 is configured to receive within the mitt opening 221. For example, the mitt opening 221 of the mitt 220 of the right wraparound portion 108 as shown and described with respect to FIG. 11 may open towards the right side of the user's body when the torso garment 140 is donned so as to receive the right hand of the user when coupling, or securing, the torso garment 140 about, or around, the user's torso. Conversely, for example, the mitt opening 221 of the mitt 220 of the left wraparound portion 107 as shown and described with respect to FIG. 10 may open towards the left side of the user's body when the torso garment 140 is donned so as to receive the left hand of the user when coupling, or securing, the torso garment 140 about, or around, the user's torso.

The size and configuration of the mitt 220 and the mitt opening 221 may provide any number of advantages. For example, the size of the mitt opening 221 may assist a user in locating, or placing, the user's hand in the mitt opening 221 when the mitt 220, and thus, the mitt opening 221, is located behind a user's back, or posterior, during donning such that, e.g., a user cannot, or may have trouble, seeing and/or reaching the mitt 220. Further, for example, the size of the mitt opening 221 may provide a large target for receiving a user's hand. Further, for example, the size of the mitt opening 221 may also allow a user to use their arm as opposed to just their fingers, or fingertips, to move the mitt 220, and thus, move the wraparound portion 210. Still further, for example, the size and configuration of the mitt 220 and the mitt opening 221 may allow variously-sized users including users having shorter arms or longer arms to reach the mitt opening 221 when donning the exemplary compression garments described herein.

The garment 200 may further include tightening apparatus 420 coupled to the wraparound portion 210 to selectively tighten the wraparound portion 210 and/or other garment portions 208 about, or around, one or more body portions of the user. More specifically, the wraparound portion 210 may define a length 229 from the proximal end region 212 to the distal end region 214 as labeled in FIG. 5, and the length 229 of the wraparound portion 210 may be adjusted using the tightening apparatus 420.

Further, the selective length 229 of the wraparound portion 210 may be described in terms of portions. For example, the wraparound portion 210 may include a first portion 442 proximate the distal end region 214 and a second portion 444 proximate the proximal end region 212. The first portion 442 may be coupled to the second portion 444 via the tightening apparatus 420. The tightening apparatus 420 may selectively bring the first portion 442 closer to the second portion 444 and may selectively allow the first portion 442 to be moved further away from the second portion 444. In other words, the first portion 442 may be moved with respect to the second portion 444 so as to adjust the length 239 of the wraparound portion 210, which in turn, may selectively tighten or loosen the garment 200 about one or more body portions of a user.

The tightening apparatus 420 may include one or more laces 430 between the proximal end region 212 and the distal end region 214. The one or more laces 430 may be described as extending back-and-forth between the first portion 442 and the second portion 444. In one or more embodiments, additional material may be located between the laces 430 and the user's skin such that, e.g., the laces 430 may not contact the user's skin, the material may provide a "buffer" between the laces 430 and the user's skin, etc. The tightening apparatus 420 may further include a tightening device 425 that may be used by a user to apply tension on the one or more laces 430 to shorten or allow the lengthening of the one or more laces 430 extending between the proximal end region 212 and the distal end region 214. In one or more embodiments, the tightening device 425 may include a spool portion rotatable about an axis to wrap, or store, a portion of the one or more laces 430 thereabout. The one or more laces 430 may be wrapped about the spool to decrease the amount of, or shorten, the laces 430 extending between the proximal end region 212 and the distal end region 214 and may be unwrapped, or unfurled, to allow the amount of laces 430 extending between the proximal end region 212 and the distal end region 214 to be increased (e.g., lengthen the laces 430). The tightening apparatus 420 is described further herein with respect to FIGS. 13A-13B.

A plan view of the exemplary head garment portion 120 including one or more head pressure applying regions 121 is shown in FIG. 7. The one or more head pressure applying regions 121 may be controllable (e.g., using controller 102 as shown in FIG. 1) to apply pressure to a portion of the head when the head garment portion 120 is positioned on the head. Further, the one or more head pressure applying regions 121 may be located in various locations within the head garment portion 120 to apply pressure to a variety of different locations on the head. For example, as described herein, the head garment portion 120 may include the right head garment portion 134 positionable proximate a right side of the head and the left head garment portion 136 positionable proximate a left side of the head. The one or more head pressure applying regions 121 associated with the right and left head garment portions 134, 136 may be controllable to apply pressure to the right and left sides of the head, respectively.

In one or more embodiments, the one or more head pressure applying regions 121 may be configured to apply pressure to a portion of the head using the one or more chambers through the control of fluid provided thereto, e.g., fluid flow, air flow, etc. For example, the head garment portion 120 may include one or more head garment ports 139 (a few of which are labeled in FIG. 7) through which fluid may be provided to the one or more chambers (e.g., such as with use of pump 103 shown in FIG. 1, under control of controller 102 with use of a sensor feedback system).

Any number of pressure applying regions 121 may be configured in the head garment portion 120 such that they may be controlled to move lymph as described, for example, with reference to FIGS. 2-4. For example, as shown in FIG. 7, four head pressure applying regions 121 are implemented. However, any number of head pressure applying regions 121 may be implemented such as, e.g., two head pressure applying regions 121, three head pressure applying regions 121, five head pressure applying regions 121, six head pressure applying regions 121, etc.

A plan view of the exemplary torso garment portion 140 including one or more torso pressure applying regions 141 are shown in FIG. 8. Although as shown the torso garment portion 140 may include eight torso pressure applying regions 141, any number of torso pressure applying regions 141 may be implemented or utilized. The one or more torso pressure applying regions 141 may be configured to be controlled (e.g., using controller 102 as shown in FIG. 1) to apply pressure to one or more portions of the torso when the torso garment portion 140 is positioned on the torso.

In one or more embodiments, each of the one or more torso pressure applying regions 141 may be configured in any suitable manner such that the regions 141 may be controlled to apply pressure to a portion of the torso to move lymph as desired. For example, the one or more torso pressure applying regions 141 may include fluid chambers or cells, pneumatic pressure applying regions, actuatable elements applying pressure to regions, hydraulic pressure applying regions, etc. Specifically, the one or more torso pressure applying regions 141 may include one or more chambers configured to receive fluid (e.g., air).

For example, in one or more embodiments, the one or more torso pressure applying regions 141 may be configured to apply pressure to a portion of the torso using the one or more chambers through the control of fluid provided thereto, e.g., liquid flow, air flow, etc. For example, the torso garment portion 140 may include one or more torso garment ports 159 (a few of which are labeled in FIG. 8) through which fluid may be provided to the one or more chambers (e.g., such as with use of pump 103 shown in FIG. 1, under control of controller 102 with use of a sensor feedback system).

In one or more embodiments (e.g., as shown in FIGS. 1 and 10-12), the right wraparound portion 108 may be configured to overlap the right lower anterior torso garment portion 144 and the left wraparound portion 107 may be configured to overlap the left lower anterior torso garment portion 148 to, e.g., further don and/or tighten or secure the torso garment portion 140 about the body 10 after, e.g., the right chest garment portion 142 is coupled to the left chest garment portion 143 as will be further described herein with respect to FIGS. 9-12. Further, in one or more embodiments and/or depending on the size of the body with respect to the size of the torso garment, the right wraparound portion 108 may be configured to overlap the midline of the torso and over to the left lower anterior torso garment portion 148, and likewise, the left wraparound portion 107 may be configured to overlap the midline of the torso to the right lower anterior torso garment portion 144.

The torso garment portion 140 may further include right and left posterior adjustment portions 190, 192 configure to adjust torso garment portion 140 to properly fit around the circumference, or bust, of the torso of the body 10 prior to donning the torso garment portion 140. The right posterior adjustment portion 190 may extend from the right lower anterior torso garment portion 144 and the left posterior adjustment portion 192 may extend from the left lower anterior torso garment portion 148 as shown in FIG. 8. The right posterior adjustment portion 190 may be configured to wrapped around the right posterior of the torso of the body 10 and be removably coupled to the left posterior adjustment portion 192, which is configured to wrapped around the left posterior of the torso of the body. The coupling of the right posterior adjustment portion 190 to the left posterior adjustment portion 192 may be defined the size around the torso about which the torso garment portion 140 may fit (e.g., to define the snugness or tightness of the torso garment portion 140 around the torso of the body 10). To facilitate or provide the coupling between the right posterior adjustment portion 190 and the left posterior adjustment portion 192, each of the right and left posterior adjustment portions 190, 192 may include hook-and-loop fasteners configured to be coupled to each other. Further, when the torso garment portion 140 is being adjusted, the right posterior adjustment portion 190 may be coupled to the left posterior adjustment portion 192 to vary the size of the torso garment portion 140. For example, the right posterior adjustment portion 190 may be pulled closer to the left posterior adjustment portion 192 when coupling for a smaller, tighter fit while the right posterior adjustment portion 190 may be located further away from the left posterior adjustment portion 192 when coupling for a larger, looser fit.

Additionally, the right posterior adjustment portion 190 and the left posterior adjustment portion 192 may be configured to be located on the "inside" of the posterior torso garment portion 150 when being donned. In one or more embodiments, the posterior torso garment portion 150 may be removably coupled to the right posterior adjustment portion 190 and the left posterior adjustment portion 192 through, e.g., hook-and-loop fasteners, so as to secure the posterior torso garment portion 150 to be located proximate the posterior of the torso of the body 10. Generally, the right posterior adjustment portion 190 and the left posterior adjustment portion 192 may be adjusted and coupled prior to coupling the posterior torso garment portion 150 thereto because, e.g., coupling of the posterior torso garment portion 150 to the right posterior adjustment portion 190 and the left posterior adjustment portion 192 may limit, or restrict, the adjustment of the right posterior adjustment portion 190 with respect to the left posterior adjustment portion 192. In other words, the coupling of the posterior torso garment portion 150 to the right posterior adjustment portion 190 and the left posterior adjustment portion 192 may further secure, or couple, the right posterior adjustment portion 190 to the left posterior adjustment portion 192 to, e.g., maintain the connection therebetween.

Figure 9:
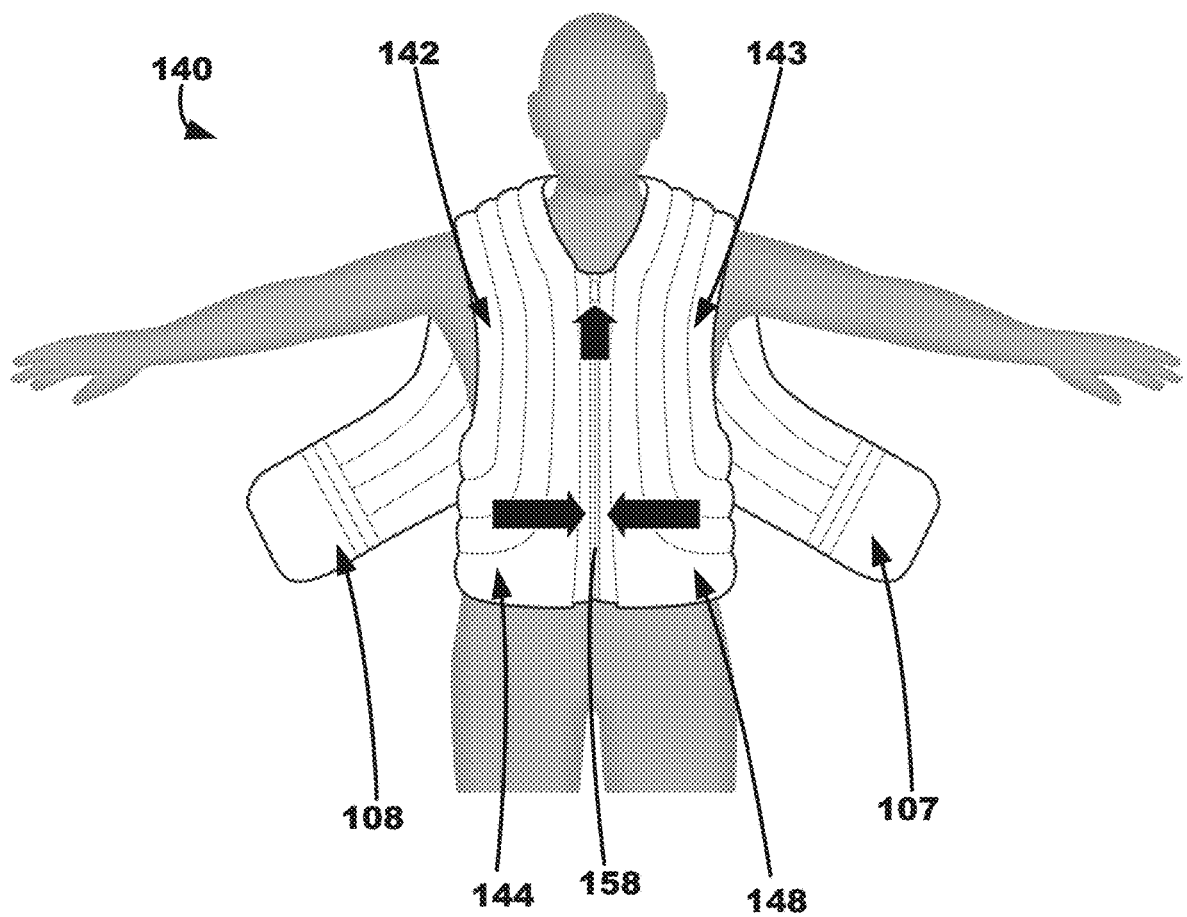
FIG. 9 is a front view of an exemplary torso garment portion being donned on the body and coupled around a body.
Figure 10:
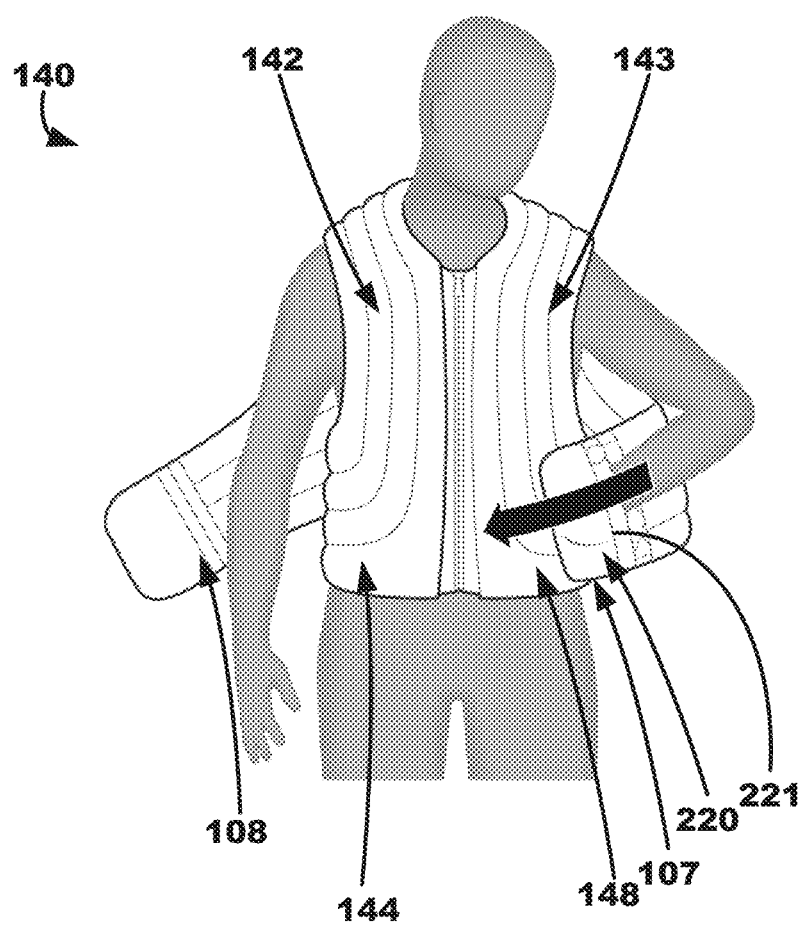
FIGS. 10-11 are front views of the torso garment portion of FIG. 9 being further coupled, or secured, around the body.
Figure 11:
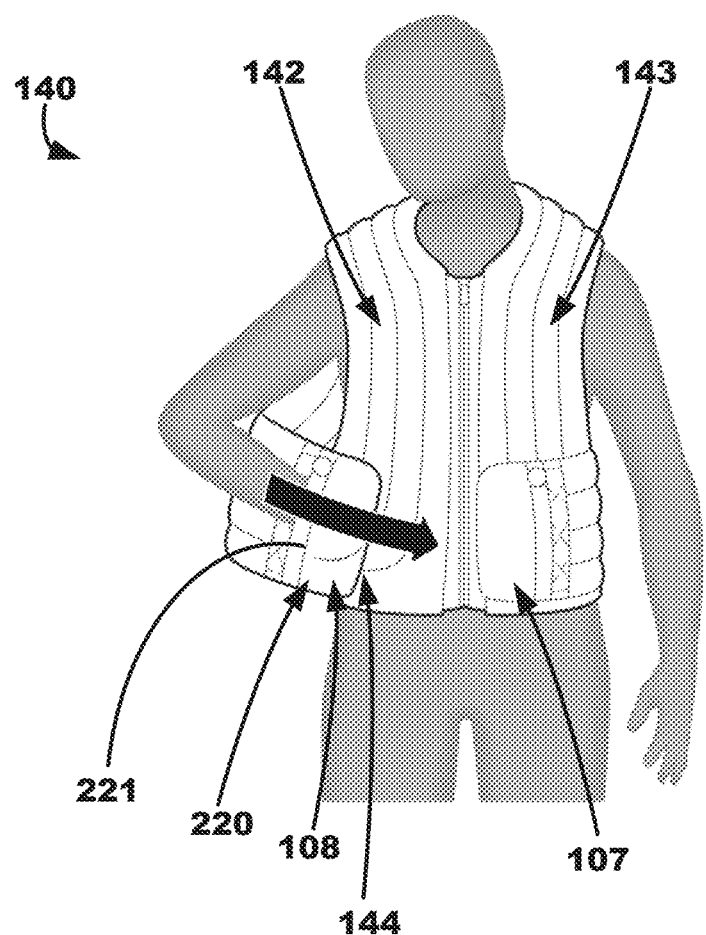

At least a portion of the donning process of the torso garment portion 140 is depicted in FIGS. 9-11. For example, the torso garment portion 140 may be located on the torso of the body 10 as shown in FIG. 9. More specifically, the neck of the body 10 may be positioned through the neck aperture and the arms of the body 10 may be positioned through the right and left arm openings 153, 154 such that the posterior, or back, of the torso is proximate, or adjacent, the posterior torso garment portion 150 and the right and left posterior adjustment portions 190, 192. The right chest garment portion 142 may be coupled to the left chest garment portion 143 using, e.g., the zipper 158.

Next, to further secure, or tighten, the torso garment portion 140 about the torso of the body 10, a user may place a hand in a mitt opening such as the left mitt opening 221 of the left wraparound portion 107 as shown in FIG. 10 and then move the left wraparound portion 107 around the left anterior of the torso over the left lower anterior garment portion 148 for coupling thereto using fastening apparatus or structures such as, e.g., hook-and-loop fasteners. The movement and coupling of the left wraparound portion 107 may tighten the torso garment portion 140 about the torso to, e.g., provide a snug fit. Likewise, a user may place a hand in a mitt opening such as the right mitt opening 221 of the right wraparound portion 108 shown in FIG. 11, and then move the right wraparound portion 108 around the right anterior of the torso over the right lower anterior garment portion 144 for coupling thereto using fastening apparatus or structures such as, e.g., hook-and-loop fasteners. The movement and coupling of the right wraparound portion 108 may further tighten the torso garment portion 140 about the torso to, e.g., provide a snug fit. In one or more embodiments, each of the mitt openings 221 may be sized, or define a size, such that a majority of not all of a human hand may fit within the mitt openings 221 so as, e.g., provide a large opening to receive a human hand when the wraparound portions 107, 108 are located in awkward position for the human user to grasp (e.g., behind or partially-behind the user's back, hanging below the user's waistline, etc.). Further, it may be described that the mitt openings 221 are part of a mitt apparatus, or mitt, located proximate the end region of the respective wraparound portion 107, 108. Still further, it may be described that the mitt apparatus, or mitt, may terminate the end regions, or the distal end regions, of the wraparound portion 107, 108. In other words, the distal end regions of the wraparound portions 107, 108 may include mitts, or mitt apparatus, which define the mitt openings 221. Additionally, as depicted on FIG. 8, the hook-and-loop fastener surface of the wraparound portions 107, 108 may include "spot welds" or "button welds" 199 to, e.g., resist the hook-and-loop fastener surface from "tenting" when attaching and unattaching the wraparound portions 107, 108 from the remainder of the torso garment portion 140.

Figure 12:
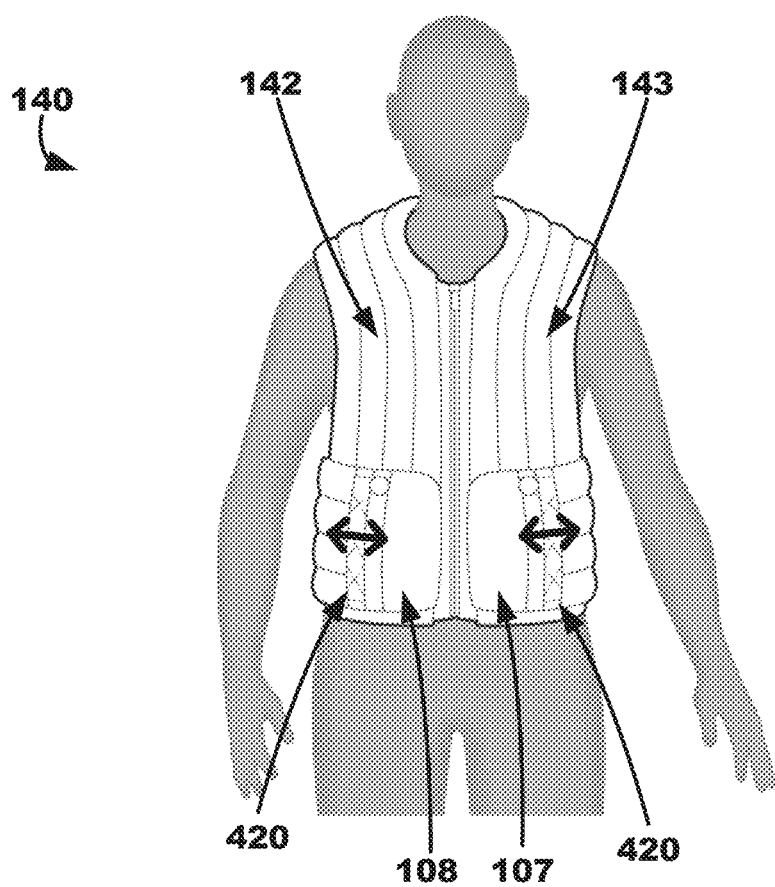
FIG. 12 is a front view of the torso garment portion of FIG. 9 after being donned and coupled to the body for tightening.

After the right wraparound portion 108 is coupled to the right lower anterior garment portion 144 as shown in FIG. 12, the torso garment portion 140 may be further tightened using tightening apparatus 420 (e.g., lacing systems). For example, as shown, tightening apparatus 420 may be part of each of the wraparound portions 107, 108 such that tightening apparatus 420 may extend or shorten the length of the wraparound portions 107, 108. Further, it may be generally described that the tightening apparatus 420 may configured to further assist in positioning (e.g., tightening) the torso garment portion 140 on the torso of the body. For example, the distal end regions of the right and left wraparound portions 108, 107 may be moved relative to the proximal end regions thereof using the tightening apparatus 420 to selectively adjust, or vary, a length of the right and left wraparound portions 108, 107 as indicated by the double-sided arrows (in FIG. 12), which will be described further herein with respect to FIG. 13.

Figure 13A:
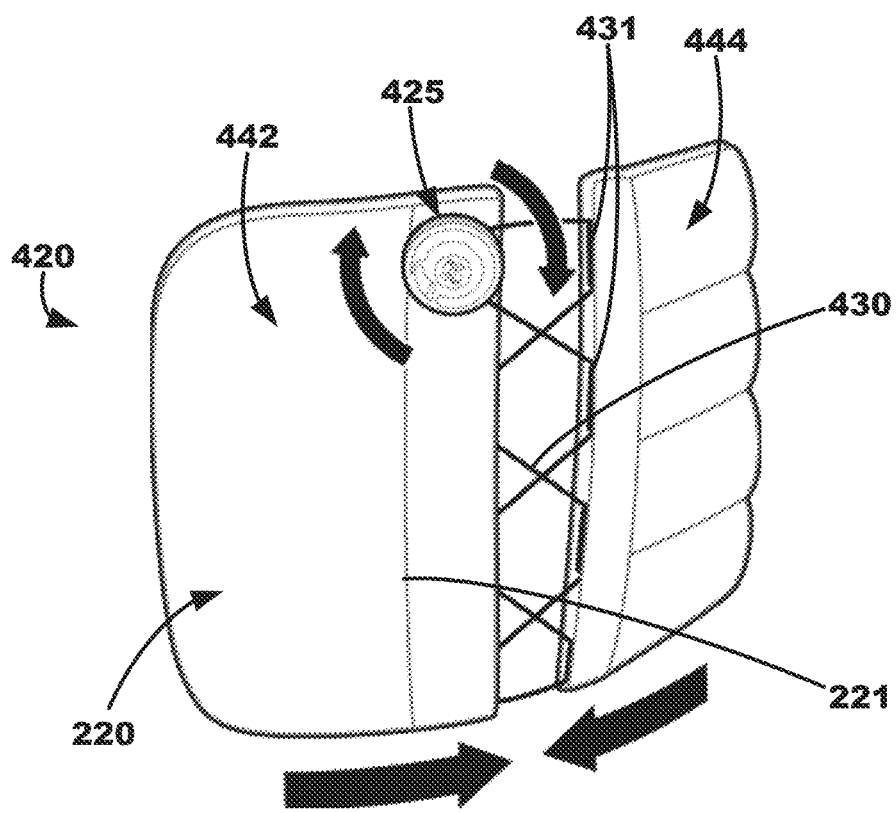
FIGS. 13A-13B are perspective views of an exemplary tightening apparatus (e.g., a lacing system) for use within the exemplary compression garments of FIGS. 1 and 5-12 to assist in donning one or more garment portions thereof.
Figure 13B:
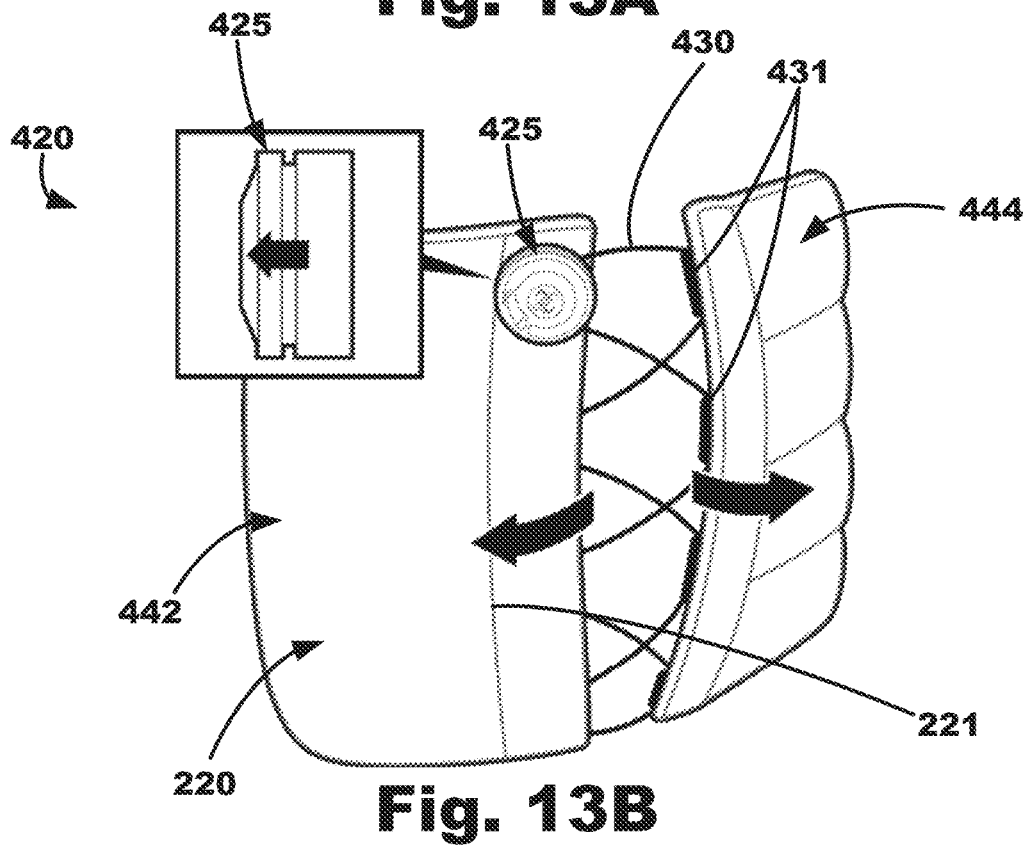

Generally, as shown in FIGS. 13A-13B, exemplary tightening apparatus 420 may be configured, or operable, to move a first portion 442 of a wraparound portion relative to a second portion 444 of the wraparound portion to, e.g., assist in tightening one or more garment portions about one or more body portions such as the torso garment portion 140 about the torso of the body. The tightening apparatus 420 may include one or more laces 430 positioned (e.g., laced) between the first and second portions 442, 444. In one or more embodiments, the one or more laces 430 may be guided between the first and second portions 442, 444 using guide members, or eyelets, 431 (a few of which are labeled in FIGS. 13A-13B).

The tightening apparatus 420 may also include a tightening device 425 that may be coupled to the one or more laces 430 and configured to apply tension on, or to, the one or more laces 430 to either shorten or lengthen the distance between the first portion 442 and the second portion 444 of the wraparound portions, e.g., to tighten the torso garment portion 140 about the torso of the body 10. In one or more embodiments, the tightening device 425 may be rotated one direction to lengthen the distance between the first portion 442 and the second portion 444 and rotated the opposite direction to shorten the distance between the first portion 442 and the second portion 444. In one or more embodiments, the tightening device 425 may be rotated one direction to shorten the distance between the first portion 442 and the second portion 444 and may be restricted from rotation in the opposite direction. For example, the tightening device 425 may define, or be configured into, a locked position, in which the tightening device 425 cannot be rotated (e.g., as shown is the zoomed in view of the tightening device 425).

The tightening apparatus 420 may be further described with respect to a working length of the one or more laces 430. The working length may be defined as the length of the one or more laces that extends back and forth between the plurality of guide members 431, which are located on, and coupled to, each of the first portion 444 and the second portion 442. The working length of the one or more laces 430 may be described as being selectively adjustable by using the tightening device 425, which in turn, may selectively adjust the length 229 of the wraparound garment portion defined from the proximal end region 212 to the distal end region 214.

Further, it may be described that the tightening device 425 may be configurable in a tightening configuration and a loosening configuration. The working length of the one or more laces 430 may be selectively shortenable and restricted from being lengthened when the tightening device 425 is configured in the tightening configuration. Further, the working length may be selectively lengthened, or extended, when the tightening device 425 is configured in the loosening configuration. As shown in FIG. 13A, the tightening device 425 is being used to shorten the working length of the one or more laces 430 thereby bringing the first portion 442 closer to the second portion 444, which may shorten, or tighten, the wraparound portion. Conversely, as shown in FIG. 13B, the tightening device 425 is being used to allow the working length of the one or more laces 430 to be lengthened thereby allowing the first portion 442 to move further away from the second portion 444, which may lengthen, or loosen, the wraparound portion.

As shown in FIGS. 1 and 9-13, the tightening device 425 is located near an upper area of the tightening apparatus 420. In one or more embodiments, the tightening device 425 may be centered vertically on the tightening apparatus 420 to, e.g., to improve lacing efficiency, ease of use, etc. In other embodiments, the tightening device 425 may located near a lower area of the tightening apparatus 420 such as shown in FIG. 8. Further, in one or more embodiments such as those depicted herein, the tightening device 425 may be located on the anterior side of the body when the exemplary garment portions are donned to, e.g., provide ease of use to the user.

As shown in FIGS. 1 and 8-11, the tightening apparatus 420 may be located proximate the left and right lower anterior garment portions 144, 148 and as part of the left and right wraparound portions 107, 108, e.g., for convenient access by the hands of a user. Also, the tightening apparatus 420 may be located in any other location along the garment that may need additional help in tightening or adjusting the garment proximate the body. The tightening apparatus 420 described herein may be similar to and include one or more features found in PCT International Application No. PCT/US2015/036951 entitled "Compression Garment System with Tightening Apparatus," which is herein incorporated by reference in its entirety.

A cross-section of a portion 800 of an exemplary garment including one or more cells 801 which may be used in providing any of the garments described herein is shown in FIG. 14. The garment portion 800 may define an exterior surface 802 configured to face the exterior, e.g., away from a user when wearing the garment portion 800, and an opposing interior surface 803 configured to face the interior, e.g., towards a user wearing the garment portion 800. The interior surface 803 may be configured to be positioned closer to the human body than the exterior surface 802 when the garment portion 800 is positioned on the body. As shown, the garment portion 800 defines a plurality of chambers configured and corresponding to pressure applying regions. Each of the chambers 801 defines a volume 805 that may be separated in any way that isolates the volume 805 of a chamber from the volumes of the other chambers 801 (e.g., such that the chambers. For example, the volumes 805 of the chambers 801 may be separated by welds 815, e.g., welds between one or more layers of the garment portion 800 as will be further described herein. The volumes, or cavities, 805 defined by, or in each, of the chambers 801 may be configured to receive a fluid. The fluid may be received from a source (e.g., from pump 103 shown in FIG. 1) to apply pressure at a pressure applying region of the garment to a body portion when garment portion 800 is worn by a user. For example, fluid may be directed to each of the volumes 805 of the chambers 801 in a sequential or non-sequential manner.

Further, each of the various pressure applying regions described herein may include, e.g., one of the one or more chambers 801 or a plurality of the chambers 801. In one or more embodiments, different pressure applying regions described herein may include, e.g., the same one or more chambers, but may, e.g., be positioned at different locations on the garment.

The garment portion 800 may include one or more layers from the exterior surface 802 to the interior surface 803. For example, the exterior facing layer 806, or the layer defining the exterior surface 802, may include one or more fabric materials so as to define a "hook" surface on the exterior surface 802 for coupling to a "loop" surface or material forming, or defining, a "hook-and-loop" fastener. The exterior surface of the exemplary garment portions described herein may be partially or completely defined by a "hook" surface for use in a "hook-and-loop" fastener.

A foam layer 807 may be adjacent the exterior facing layer 807, and then a polymer layer 808 (e.g., polyurethane, polyvinyl, etc.) may be located adjacent the foam layer 807 facing the volume 803 of the chamber 801. The interior side of the garment portion 800 may be similar to the exterior side except that, instead of a exterior facing layer, the foam layer 807 may be adjacent a fabric layer 809 configured to be located adjacent the torso of a body.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

Particular materials and dimensions thereof recited in the disclosed examples, as well as other conditions and details, should not be construed to unduly limit this disclosure. Although the subject matter has been described in language specific to structural features and/or methodological acts, it is to be understood that the subject matter defined in the appended claims is not necessarily limited to the specific features or acts described above. Rather, the specific features and acts described above are disclosed as representative forms of implementing the claims.

What is claimed is:

1. A compression garment comprising:
a head garment configured to be positioned around both sides of a head of a body from a posterior of the head to an anterior of the head, wherein the head garment comprises a plurality of controllable head pressure applying regions positionable proximate at least cheeks and a posterior of the head, each of the plurality of controllable head pressure applying regions comprising one or more cells configured to receive a fluid, wherein, during use, one cell of the one or more cells of the head garment extends forward from a posterior portion of the head garment toward a forward portion of the head garment, and further angles downward from the forward portion of the head garment to a cheek portion of the head garment, the head garment further comprising a forehead garment portion positionable proximate a forehead of the head, wherein the forehead garment portion comprises one or more forehead connection straps configured for use in donning the head garment on the head.

2. The compression garment of claim 1, wherein the compression garment is controllable by a controller configured to control each of the plurality of controllable head pressure applying regions to apply pressure to the cheeks and the posterior of the head to move lymph at least from the cheeks towards a neck of the head.

3. The compression garment of claim 1, wherein the head garment defines one or more head open regions proximate a top portion of the head.

4. The compression garment of claim 1, wherein the head garment comprises an under chin garment portion positionable proximate under a chin of the head, wherein the plurality of controllable head pressure applying regions comprises one or more under chin pressure applying regions at the under chin garment portion, the one or more under chin pressure applying regions controllable to apply pressure to a portion under the chin.

5. The compression garment of claim 1, wherein the head garment comprises one or more nasal connection straps positionable proximate a nasal bridge of the head, wherein the one or more nasal connection straps are configured to connect a right head garment portion of the head garment and a left head garment portion of the head garment.

6. The compression garment of claim 1, wherein at least a portion of the plurality of controllable head pressure applying regions define an arcuate shape.

7. A compression garment system comprising:
a head garment comprising a plurality of head pressure applying regions controllable to apply pressure to a plurality of portions of a head of a body, wherein the plurality of head pressure applying regions are positioned in a concentric pattern radiating away from a face of the head of the body to apply pressure to the plurality of portions of the head of the body to move lymph from portions of the head proximate the face to a neck of the body, the head garment further comprising a forehead garment portion positionable proximate a forehead of the head, wherein the forehead garment portion comprises one or more forehead connection straps configured for use in donning the head garment on the head, and
a controller operably coupled to the head garment to control pressure applied by the plurality of head pressure applying regions.

8. The compression garment system of claim 7, wherein the controller is further configured to apply pressure to the plurality of portions of the head using the plurality of head pressure applying regions using a head pressure application sequence, wherein the head pressure application sequence comprises application of increased pressure sequentially to portions of the plurality of portions of the head closest to the face of the head to portions of the plurality of portions of the head further away from the face of the head and closest the neck of the body.

9. The compression garment system of claim 7, wherein the head garment comprises a plurality of head cells corresponding to the plurality of head pressure applying regions and configured to receive fluid to apply pressure to the plurality of portions of the head when the head garment is donned.

10. The compression garment system of claim 7, wherein the head garment defines one or more head open regions proximate a top portion of the head.

11. The compression garment system of claim 7, wherein the head garment comprises an under chin garment portion positionable proximate under a chin of the head, wherein the plurality of head pressure applying regions comprises one or more under chin pressure applying regions at the under chin garment portion, the one or more under chin pressure applying regions controllable to apply pressure to a portion under the chin.

12. The compression garment system of claim 7, wherein the head garment comprises one or more nasal connection straps positionable proximate a nasal bridge of the head, wherein the one or more nasal connection straps are configured to connect a right head garment portion of the head garment and a left head garment portion of the head garment.

13. The compression garment system of claim 7, wherein at least a portion of the plurality of head pressure applying regions define an arcuate shape.

\* \* \* \* \*